United States Patent
Bastos et al.

(10) Patent No.: US 10,017,503 B2
(45) Date of Patent: Jul. 10, 2018

(54) COMPOUNDS, COMPOSITIONS, AND METHODS FOR INCREASING CFTR ACTIVITY

(71) Applicant: Proteostasis Therapeutics, Inc., Cambridge, MA (US)

(72) Inventors: Cecilia M. Bastos, South Grafton, MA (US); Benito Munoz, Newtonville, MA (US); Bradley Tait, Malden, MA (US)

(73) Assignee: Proteostasis Therapeutics, Inc., Boston, MA (US)

(*) Notice: Subject to any disclaimer, the term of this patent is extended or adjusted under 35 U.S.C. 154(b) by 0 days.

(21) Appl. No.: 15/653,934

(22) Filed: Jul. 19, 2017

(65) Prior Publication Data

US 2018/0127400 A1    May 10, 2018

Related U.S. Application Data

(63) Continuation of application No. 15/125,830, filed as application No. PCT/US2015/020499 on Mar. 13, 2015, now Pat. No. 9,745,292.

(60) Provisional application No. 62/102,202, filed on Jan. 12, 2015, provisional application No. 62/096,398, filed on Dec. 23, 2014, provisional application No. 61/952,424, filed on Mar. 13, 2014.

(51) Int. Cl.

| | |
|---|---|
| *C07D 413/12* | (2006.01) |
| *C07D 417/12* | (2006.01) |
| *A61K 31/422* | (2006.01) |
| *A61K 31/433* | (2006.01) |
| *A61K 45/06* | (2006.01) |
| *A61K 31/506* | (2006.01) |
| *A61K 31/4439* | (2006.01) |

(52) U.S. Cl.
CPC .......... *C07D 413/12* (2013.01); *A61K 31/422* (2013.01); *A61K 31/433* (2013.01); *A61K 31/4439* (2013.01); *A61K 31/506* (2013.01); *A61K 45/06* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,780,393 | A | 7/1998 | Newton |
| 5,888,941 | A | 3/1999 | Bartroli et al. |
| 7,846,951 | B2 | 12/2010 | Miller et al. |
| 7,915,297 | B2 | 3/2011 | Cho et al. |
| 7,981,935 | B2 | 7/2011 | Olson et al. |
| 8,193,225 | B2 | 6/2012 | Schneider et al. |
| 8,236,838 | B2 | 8/2012 | Jones et al. |
| 8,623,860 | B2 | 1/2014 | Fleck et al. |
| 8,815,924 | B2 | 8/2014 | Dorsch et al. |
| 9,745,292 | B2 | 8/2017 | Bastos et al. |
| 9,790,219 | B2 | 10/2017 | Bastos et al. |
| 2006/0041006 | A1 | 2/2006 | Ibrahim et al. |
| 2006/0100226 | A1 | 5/2006 | Sikorski et al. |
| 2008/0090882 | A1 | 4/2008 | Dorsch et al. |
| 2009/0069288 | A1 | 3/2009 | Breinlinger et al. |
| 2009/0163545 | A1 | 6/2009 | Goldfarb |
| 2009/0264486 | A1 | 10/2009 | Jones et al. |
| 2009/0318429 | A1 | 12/2009 | Doyle et al. |
| 2010/0234367 | A1 | 9/2010 | Nomura et al. |
| 2011/0003784 | A1 | 1/2011 | Garvey et al. |
| 2011/0082181 | A1 | 4/2011 | Seiders et al. |
| 2011/0212975 | A1 | 9/2011 | Kao et al. |
| 2012/0095002 | A1 | 4/2012 | Ratcliffe et al. |
| 2012/0264738 | A1 | 10/2012 | Sugimoto et al. |
| 2013/0217883 | A1 | 8/2013 | Adaway |
| 2013/0237502 | A1 | 9/2013 | Curtis et al. |
| 2014/0364467 | A1 | 12/2014 | Schneider et al. |
| 2016/0151335 | A1 | 6/2016 | Tait et al. |
| 2017/0001991 | A1 | 1/2017 | Bastos et al. |
| 2017/0001993 | A1 | 1/2017 | Bastos et al. |
| 2017/0233379 | A1 | 8/2017 | Bastos et al. |
| 2017/0362214 | A1 | 12/2017 | Bastos et al. |
| 2017/0369480 | A1 | 12/2017 | Bastos et al. |
| 2017/0369482 | A1 | 12/2017 | Bastos et al. |

FOREIGN PATENT DOCUMENTS

| | | |
|---|---|---|
| CA | 2736441 A1 | 10/2012 |
| EP | 0337263 A2 | 10/1989 |
| EP | 0957099 A2 | 11/1999 |
| JP | 2006176443 A | 7/2006 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |

(Continued)

OTHER PUBLICATIONS

"AID 775-Screen for Chemicals that Extend Yeast Lifespan," PubChem, 1-11 (Jul. 12, 2007), XP055331102.
Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands,"Journal of Medicinal Chemistry, 57:10 4239-4251(2014), XP002754990.
CAS Registry No. 797781-85-2 (available Dec. 15, 2004).
Chang, X., "3-(2-chlorophenyl)-N-methylisoxazole-5-Carboxamide," ACTA Crystallographica, Section E: Structure Reports Online, vol. E63(7), pp. o3074-sup-7 (2007).

(Continued)

*Primary Examiner* — Kamal Saeed
(74) *Attorney, Agent, or Firm* — Goodwin Procter LLP

(57) ABSTRACT

The disclosure encompasses compounds having e.g., Formula (Ia) or (Ib), compositions thereof, and methods of modulating CFTR activity. The disclosure also encompasses methods of treating a condition associated with CFTR activity or condition associated with a dysfunction of proteostasis comprising administering to a subject an effective amount of a compound of Formula (I) or (Ib).

28 Claims, No Drawings

(56) References Cited

FOREIGN PATENT DOCUMENTS

| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |

OTHER PUBLICATIONS

Compound Summary for CID 70741394, PUBCHEM: Create Date: Mar. 4, 2013 [retrieved on May 12, 2015].

Compound Summary for CID 70756362, PUBCHEM: Create Date: Mar. 4, 2013 [retrieved on May 12, 2015].

Compound Summary for: CID 36257620, PUBCHEM: Create Date: May 29, 2009 [retrieved on May 12, 2015].

Compound Summary for: CID 55795703, PUBCHEM: Create Date: Jan. 25, 2012 [retrieved on May 12, 2015].

Demina et al., "5-substituted Pyridylisoxazoles as Effective Inhibitors of Platelet Aggregation," Russian Chemical Bulletin, International Edition, vol. 63(2) 2095-2113 (2014).

International Search Report and Written Opinion for International Application No. PCT/US2014/044100, dated Oct. 10, 2014, 8 pages.

International Search Report and Written Opinion for International Application No. PCT/US2015/000189, dated Mar. 18, 2016, 10 pages.

International Search Report and Written Opinion for International Application No. PCT/US2015/000202, dated Mar. 22, 2016, 8 pages.

International Search Report and Written Opinion for International Application No. PCT/US2015/000211, dated Mar. 29, 2016, 10 pages.

International Search Report and Written Opinion for International Application No. PCT/US2015/000212, dated Jul. 1, 2016, 22 pages.

International Search Report and Written Opinion for International Application No. PCT/US2015/020460, dated Jun. 9, 2015, 7 pages.

International Search Report and Written Opinion for International Application No. PCT/US2015/020499, dated Jun. 9, 2015, 8 pages.

International Search Report and Written Opinion for International Application No. PCT/US2015/036691, dated Aug. 20, 2015, 12 pages.

International Search Report and Written Opinion for International Application No. PCT/US2016/012982, dated Mar. 7, 2016, 12 pages.

International Search Report and Written Opinion for International Application No. PCT/US2016/043835, dated Oct. 10, 2016, 8 pages.

Kalid et al., "Small Molecule Correctors of F508del-CFTR Discovered by Structure-based Virtual Screening," Journal of Computer-Aided Molecular Design, vol. 24:971-991 (2010).

Lack et al., "Targeting the Binding Function 3 (BF3) Site of the Human Androgen Receptor through Virtual Screening," Journal of Medicinal Chemistry, vol. 54(24) 8563-8573 (2011).

Liedtke, W., "Role of TRPV ion Channels in Sensory Transduction of Osmotic Stimuli in Mammals," Experimental Physiology, 92:3 507-512 (2007) XP055252392.

Lukevics et al.,"Synthesis and Cytotoxicity of Silyl- and Carbonyl—substituted Isoxazoles," Chemistry of Heterocyclic Compounds, Springer New York LLC, vol. 36(10); 1226-1231 (1995).

Munchhof et al., "Discovery of PF-04449913, a Potent and Orally Bioavailable Inhibitor of Smoothened," ACS Medicinal Chemistry Letters, vol. 3(2) 106-111 (2012).

Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.

Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).

Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).

Supplemental European Search Report dated Jan. 9, 2017 in European Patent No. 14816975.8 (19 pages).

Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].

U.S. Appl. No. 14/900,345, published as US 2016-0151335 A1 on Jun. 2, 2016, Methods of Modulating CFTR Activity, filed Dec. 21, 2015.

U.S. Pat. No. 9,790,219, issued on Oct. 17, 2017, U.S. Appl. No. 15/125,827; published as US 2017-0001993 A1 on Jan. 5, 2017, Compounds, Compositions and Methods for Increasing CFTR Activity, filed Sep. 13, 2016.

U.S. Appl. No. 15/697,901, Compounds, Compositions and Methods for Increasing CFTR Activity, filed Sep. 7, 2017.

U.S. Pat. No. 9,745,292, issued on Aug. 29, 2017, U.S. Appl. No. 15/125,830; published as US 2017-0001991 A1 on Jan. 5, 2017, Compounds, Compositions and Methods for Increasing CFTR Activity, filed Sep. 13, 2016.

U.S. Appl. No. 15/320,172, published as US 2017-0233379 A1 on Aug. 17, 2017, Compounds, Compositions and Methods for Increasing CFTR Activity, filed Dec. 19, 2016.

U.S. Appl. No. 15/539,392, published as US 2017-0369480 A1 on Dec. 28, 2017, Compounds, Compositions and Methods for Increasing CFTR Activity, filed Jun. 23, 2017.

U.S. Appl. No. 15/539,397, published as US 2017-0369482 A1 on Dec. 28, 2017, Derivatives of 5-Phenyl- or 5-Heteroarylathiazol-2-Carboxylic Amide Useful for the Treatment of Inter Alia Cystic Fibrosis, filed Jun. 23, 2017.

U.S. Appl. No. 15/539,401, Derivatives of 5-(Hetero)Arylpyrazol-3-Carboxylic Amide or 1-(Hetero)Aryltriazol-4-Carboxylic Amide Useful for the Treatment of Inter Alia Cystic Fibrosis, filed Jun. 23, 2017.

U.S. Appl. No. 15/539,405, published as US 2017-0362214 A1 on Dec. 21, 2017, Derivatives of 3-Heteroarylisoxazol-5-Carboxylic Amide Useful for the Treatment of Inter Alia Cystic Fibrosis, filed Jun. 23, 2017.

U.S. Appl. No. 15/542,997, Compunds, Compositions and Methods for Increasing CFTR Activity, filed Jul. 12, 2017.

COMPOUNDS, COMPOSITIONS, AND METHODS FOR INCREASING CFTR ACTIVITY

CROSS-REFERENCE TO RELATED APPLICATIONS

This application is a continuation of U.S. patent application Ser. No. 15/125,830, filed Sep. 13, 2016, which is a national stage filing under 35 U.S.C. § 371 of PCT/US2015/020499, filed on Mar. 13, 2015, which claims the benefit of United States ("U.S.") Provisional Application No. 61/952,424, filed on Mar. 13, 2014; U.S. Provisional Application No. 62/096,398, filed on Dec. 23, 2014; and U.S. Provisional Application No. 62/102,202, filed on Jan. 12, 2015; each of these prior applications is incorporated herein by reference in its entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis ($Cl^-$, $Na^+$, $HCO_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7(6): e39809.doi: 10.1371/journal. pone.0039809; Bombieri et al. (2011), J Cyst Fibros. 2011 June; 10 Suppl 2:S86-102; (Albert et al. (2008). Clinical Respiratory Medicine, Third Ed., Mosby Inc.; Levin et al. (2005), Invest Ophthalmol Vis Sci., 46(4):1428-34; Froussard (2007), Pancreas 35(1): 94-5).

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds such as those having Formula (Ia) and (Ib) can increase cystic fibrosis transmembrane conductance regulator (CFTR) activity as measured in human bronchial epithelial (hBE) cells.

Disclosed herein are compounds such as those having the Formula (Ia) or (Ib):

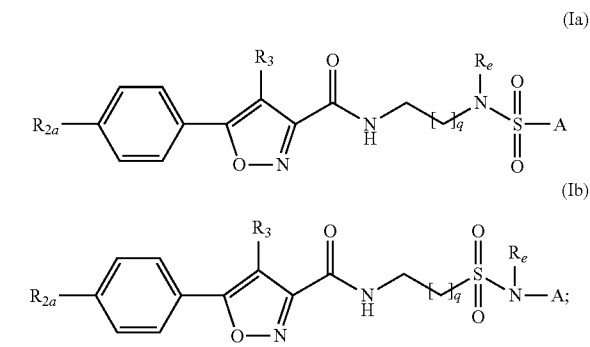

or a pharmaceutically acceptable salt, prodrug or solvate thereof, wherein:
$R_{2a}$ is hydrogen or fluoro;
$R_3$ is hydrogen or fluoro;
A is an optionally substituted 5- or 6-membered heteroaryl;
each $R_e$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and q is 1 or 2.

Also disclosed herein are compounds such as those having the Formula (II):

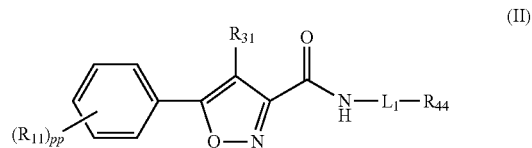

or a pharmaceutically acceptable salt, prodrug or solvate thereof, wherein
pp is 1, 2, or 3;
$R_{11}$ is independently selected for each occurrence from the group consisting of hydrogen, halogen, $C_{1-4}$ alkyl (optionally substituted by one, two or three halogens);
$R_{31}$ is selected from the group consisting of hydrogen, halogen, and $C_{1-4}$ alkyl;
$L_1$ is selected from the group consisting of $C_{2-3}$ alkylene-$NR_{hh}$—S(O)$_w$- and —$C_{1-3}$ alkylene-S(O)$_w$—$NR_{hh}$—, wherein w is 0, 1, or 2, and $L_1$ may be optionally substituted by one, two or three substituents selected from the group consisting of halogen, hydroxyl, $C_{1-3}$ alkyl (optionally substituted by one, two or three substituents each selected independently from $R_{ff}$);
$R_{44}$ is selected from the group consisting of heterocycle and a 5-6 membered monocyclic heteroaryl having one, two or three heteroatoms each selected from O, N, and S; wherein the heterocycle and the heteroaryl may be each optionally substituted by one or two substituents each selected independently from the group consisting of halogen, hydroxyl, $C_{1-6}$ alkyl, $C_{1-6}$ alkoxy, $C_{2-6}$ alkenyl, $C_{2-6}$ alkynyl, and $C_{3-7}$ cycloalkyl, wherein each of $C_{1-6}$ alkyl, $C_{1-6}$ alkoxy, $C_{2-6}$ alkenyl, $C_{2-6}$ alkynyl, and $C_{3-7}$ cycloalkyl may be optionally substituted by one, two or three substituents each independently selected from $R_{gg}$;
$R_{gg}$ is selected from the group consisting of halogen, $C_{1-6}$ alkyl, $C_{1-6}$ alkoxy, hydroxyl, C(O)OH, —C(O)O$C_{1-6}$ alkyl, —O—$C_{3-6}$ cycloalkyl, —O-heterocycle, —O-heteroaryl, —O-phenyl, —NR'R", —NR'—S(O)$_w$—$C_{1-3}$ alkyl, S(O)$_w$—NR'R", and —S(O)w-$C_{1-3}$ alkyl;
$R_{ff}$ is selected for each occurrence from group consisting of halogen, hydroxyl, $C_{1-4}$ alkyl, $C_{1-4}$ alkoxy, $C_{2-4}$ alkenyl, $C_{3-6}$ cycloalkyl, —NR'R", —NR'—S(O)$_w$—$C_{1-3}$ alkyl, S(O)$_w$—NR'R", and —S(O)$_w$—$C_{1-3}$ alkyl, where w is 0, 1, or 2, wherein $C_{1-4}$ alkyl, $C_{1-4}$ alkyoxy, $C_{2-4}$ alkenyl and $C_{3-6}$ cycloalkyl may be optionally substituted by one, two or three substituents each independently selected from the group consisting of halogen, hydroxyl, —NR'R", —NR'—S(O)$_w$—$C_{1-3}$ alkyl, S(O)$_w$—NR'R", and —S(O)w-$C_{1-3}$ alkyl;
$R_{hh}$ is selected for each occurrence from the group consisting of H, $C_{1-6}$ alkyl and $C_{3-6}$ cycloalkyl; and
R' and R" are each independently selected for each occurrence from H and $C_{1-4}$ alkyl or taken together with the nitrogen to which they are attached form a heterocyclic ring.

Also contemplated herein are pharmaceutical compositions that include a disclosed compound such as those compounds having Formula (Ia) or (Ib) or (II) and a pharmaceutically acceptable carrier or excipient.

In additional embodiments, a method of increasing cystic fibrosis transmembrane conductance regulator (CFTR) activity in a subject in need thereof is provided comprising administering to said subject an effective amount of a compound of Formula (Ia) or (Ib).

In yet additional aspects, the disclosure is directed to treating a patient suffering from cystic fibrosis comprising administering to said patient an effective amount of a disclosed compound.

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X and Δ508F) are enhanced (e.g., increased).

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein having the Formula (Ia) or (Ib) or (II), or a pharmaceutically acceptable salt, prodrug or solvate thereof, pharmaceutical compositions, methods of increasing CFTR activity and methods of treating cystic fibrosis.

In certain aspects, the compound has the Formula (Ia).

In additional embodiments, the compound has the Formula (Ib).

In yet additional embodiments, the compound has the Formula (Ia) or (Ib), wherein q is 1.

In further embodiments, the compound has the Formula (Ia) or (Ib), wherein q is 2.

In some embodiments, the compound has the Formula (Ia) or (Ib), wherein $R_3$ is hydrogen.

In additional embodiments, the compound has the Formula (Ia) or (Ib), wherein $R_3$ is fluoro.

In additional embodiments, the compound has the Formula (Ia) or (Ib), wherein $R_{2a}$ is hydrogen. In yet additional embodiments, the compound has the Formula (Ia) or (Ib), wherein $R_{2a}$ is fluoro.

In some embodiments, the compound has the Formula (Ia) or (Ib), wherein A is an optionally substituted 5- or 6-membered heteroaryl containing one or more ring nitrogen atoms, and optionally further including one or more additional ring heteroatoms.

In additional embodiments, the compound has the Formula (Ia) or (Ib), wherein A is selected from the group consisting of furanyl, pyridinyl, pyrazinyl, pyridazinyl, pyrazolyl, imidazolyl, isoxazolyl, isothiazolyl, thiadiazolyl, triazolyl, thiazolyl, oxadiazolyl, thienyl, and benzimidazolyl, each optionally substituted. In some embodiments, A is an optionally substituted imidazolyl or optionally substituted pyrazolyl.

In yet additional embodiments, A is a 5- or 6-membered heteroaryl optionally substituted with one to four $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, C(O)O$R_c$, C(O)$R_c$, C(O)C(O)$R_c$ and S(O)$_n$$R_c$; wherein each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and each n is independently 0, 1 or 2.

In further aspects, a disclosed compound has the Formula (Ia) or (Ib), wherein A is a 5- or 6-membered heteroaryl substituted with one to four $R_7$ groups, wherein each $R_7$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, halo, $OR_c$, $NR_dR_d$, $S(O)_nR_c$, $C(O)OR_c$, $NO_2$, CN and $C(O)R_c$, and wherein said 5- or 6-membered heteroaryl is optionally further substituted; wherein $R_c$ and n are as defined above, and each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl.

In some embodiments, at least one $R_7$ is selected from the group consisting of optionally substituted $C_1$-$C_{10}$ alkyl, optionally substituted $C_3$-$C_{12}$ cycloalkyl, and $OR_c$, wherein $R_c$ is an optionally substituted $C_1$-$C_{10}$ alkyl.

In additional embodiments, at least one $R_7$ is $C_1$-$C_4$ alkyl or $C_3$-$C_7$ cycloalkyl, wherein the $C_1$-$C_4$ alkyl and $C_3$-$C_7$ cycloalkyl are each optionally substituted with one or more groups selected from $OR_f$, $NR_gR_g$, and $SR_h$, wherein each of $R_f$ and $R_h$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and each $R_g$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl; or alternatively, two geminal $R_g$ groups are taken together with the nitrogen atom to which they are attached to form an optionally substituted heterocyclic or an optionally substituted heteroaryl. In further aspects, at least one $R_7$ is $C_1$-$C_4$ alkyl optionally substituted with $OR_f$, wherein $R_f$ is selected from the group consisting of hydrogen, optionally substituted $C_1$-$C_{10}$ alkyl, and optionally substituted $C_3$-$C_{12}$ cycloalkyl. In certain aspects, $R_f$ is hydrogen or optionally substituted $C_1$-$C_4$ alkyl. In yet additional embodiments, at least one $R_7$ is a $C_1$-$C_4$ alkyl substituted with one or more halo, and optionally further substituted. In additional aspects, at least one $R_7$ is a $C_1$-$C_4$ alkyl substituted with one or more fluoro, and optionally further substituted.

In yet an additional embodiment, the compound has the Formula (Ia) or (Ib), wherein A is a 5- or 6-membered heteroaryl substituted with at least one $R_8$ group having the structure:

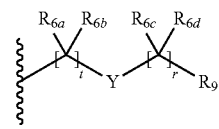

wherein $R_{6a}$, $R_{6b}$, $R_{6c}$, and $R_{6d}$ are each independently selected from the group consisting of hydrogen, optionally substituted $C_1$-$C_{10}$ alkyl and optionally substituted $C_3$-$C_{12}$ cycloalkyl; or alternatively, a geminal $R_{6a}$ and $R_{6b}$, or a geminal $R_{6c}$ and $R_{6d}$, can each independently be taken together with the carbon atom to which they are attached to form an optionally substituted $C_3$-$C_{12}$ cycloalkyl or an optionally substituted heterocyclic; Y is O, S or $NR_i$; t and r are each independently 0, 1, 2 or 3; $R_9$ is selected from the group consisting of optionally substituted $C_1$-$C_{10}$ alkyl and optionally substituted $C_3$-$C_{12}$ cycloalkyl, optionally substituted heterocyclic, optionally substituted aryl, and optionally substituted heteroaryl; and $R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl, and wherein the 5- or 6-membered heteroaryl is optionally further substituted. In some embodiments, the geminal $R_{6a}$ and $R_{6b}$ can be taken together with the carbon atom to which they are attached to form an optionally substituted $C_3$-$C_7$ cycloalkyl or an optionally substituted 3- to 7-membered heterocyclic, and/or a geminal $R_{6c}$ and $R_{6d}$ can be taken together with the carbon atom to which they are attached to form an optionally substituted $C_3$-$C_7$ cycloalkyl or an optionally substituted 3- to 7-membered heterocyclic. In yet additional embodiments, t and r are each independently 0, 1 or 2.

In certain aspects, the compound has the Formula (II) as described above. For example, in certain embodiments, a disclosed compound may be represented by the Formula (II), and $R_{44}$ is selected from the group consisting of:

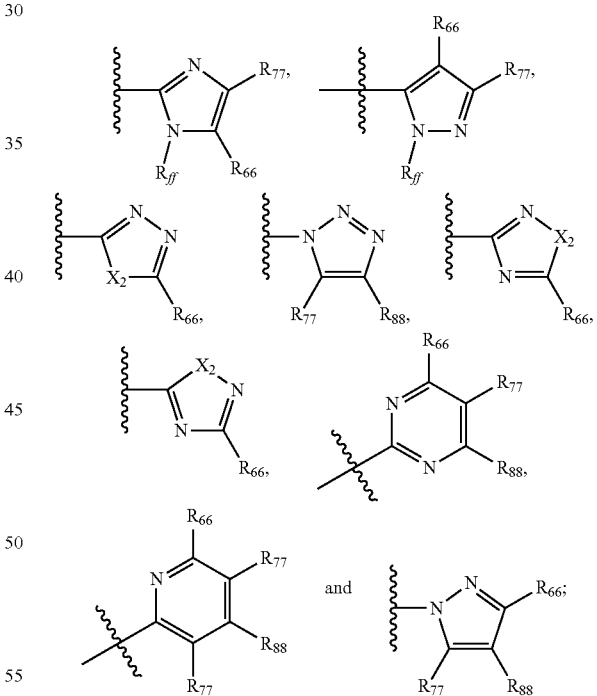

wherein $X_2$ independently for each occurrence is selected from the group consisting of O, S or $NR_{hh}$; and each $R_{66}$, $R_{77}$ and $R_{88}$ is independently selected for each occurrence from H, halogen, hydroxyl, and $C_{1-6}$ alkyl, wherein $C_{1-6}$ alkyl is optionally substituted by one, two or three substituents each independently selected from the group consisting of hydroxyl or $C_{1-6}$ alkoxy.

In certain embodiments, the compound has the Formula (II), and $R_{44}$ is 5 or 6 (e.g., 5) membered heteroaryl having one or two nitrogens (and optional an additional heteroatom selected from O and S), and wherein $R_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy. In other embodiments, $R_{44}$ is an unsubstituted 6 membered heteroaryl having one or two nitrogens (e.g., pyridyl, pyrimidinyl) or a 6 membered heteroaryl having one or two nitrogens (e.g., pyridyl, pyrimidinyl) substituted in the manner described above.

In certain embodiments, the compound has the Formula (II), and $R_{11}$ for each occurrence is H.

In certain embodiments, the compound has the Formula (II), and $R_{31}$ is H. In certain embodiments, the compound has the Formula (II), and $L_1$ is $C_{2-3}$ alkylene-NH—S(O)$_2$- or —$C_{1-3}$ alkylene-S(O)$_2$—NH—.

Exemplary compounds of the disclosure are Compounds B 1 to B 11 shown below in Table 1:

TABLE 1

| Compound | |
|---|---|
| B1 | |
| B2 (Example 2) | |
| B3 (Example 4) | |
| B4 (Example 5) | |
| B5 (Example 6) | |
| B6 (Example 7) | |

TABLE 1-continued

Compound

B7
(Example 8)

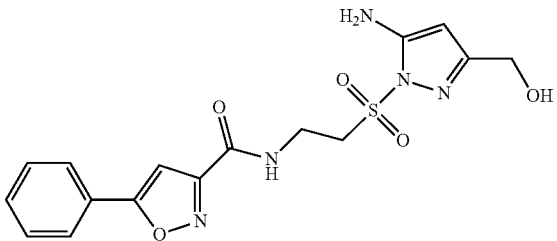 [SMILES: Nc1cc(CO)nn1S(=O)(=O)CCNC(=O)c1cc(-c2ccccc2)on1]

B8
(Example 9)

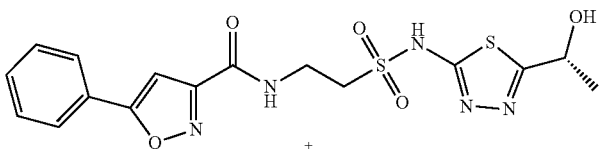

+

B9
(Example 9)

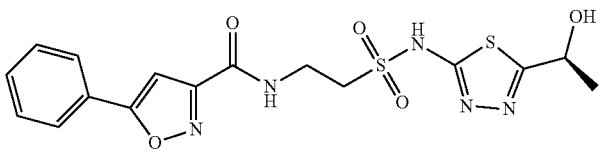 [SMILES: C[C@H](O)c1nnc(NS(=O)(=O)CCNC(=O)c2cc(-c3ccccc3)on2)s1]

B10
(Example 1)

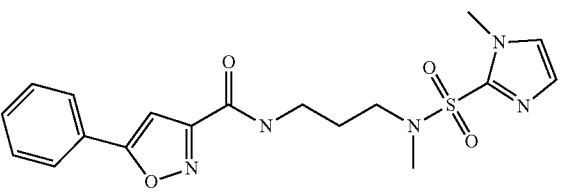 [SMILES: CN(CCCNC(=O)c1cc(-c2ccccc2)on1)S(=O)(=O)c1nccn1C]

B11
(Example 3)

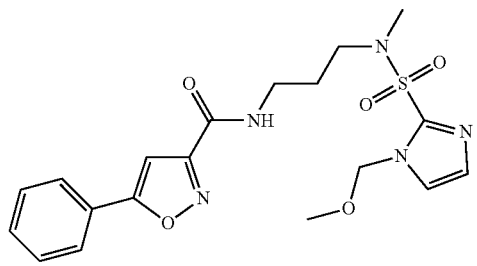 [SMILES: COCn1ccnc1S(=O)(=O)N(C)CCCNC(=O)c1cc(-c2ccccc2)on1]

In yet additional embodiments, provided herein is a pharmaceutical composition comprising a contemplated compound, for example, a compound of Formula (Ia) or (Ib) or (II), and a pharmaceutically acceptable carrier or excipient.

It is to be understood that the specific embodiments described herein can be taken in combination with other specific embodiments delineated herein. For example, as discussed above, in some embodiments, $R_{2a}$ is fluoro, and in some embodiments described above, A is an optionally substituted imidazolyl or pyrazolyl. For example, a compound of Formula (Ia) or (Ib), wherein $R_{2a}$ is fluoro and A is an optionally substituted imidazolyl, thiadiazole, pyrimidinyl, pryidinyl, or pyrazolyl is contemplated.

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the present invention herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylbutyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$ alkenyl, and $C_{3-4}$ alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively for example. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$ alkoxy, and $C_{2-6}$ alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring, a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclic rings may be linked to the adjacent radical through carbon or nitrogen. Examples of heterocyclic groups include, but are not limited to, pyrrolidine, piperidine, morpholine, thiomorpholine, piperazine, oxetane, azetidine, tetrahydrofuran or dihydrofuran etc.

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, naphthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "substituted" refers to substitution by independent replacement of one, two, or three or more of the hydrogen atoms with substituents including, but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —$C(O)R_y$, —$C(O)C(O)R_y$, —$OCO_2R_y$, —$OC(O)R_y$, $OC(O)C(O)R_y$, —$NHC(O)R_y$, —$NHCO_2R_y$, —$NHC(O)C(O)R_y$, NHC(S)$NH_2$, —NHC(S) $NHR_x$, —NHC(NH)$NH_2$, —NHC(NH)$NHR_x$, —NHC(NH) $R_x$, —C(NH)$NHR_x$, and (C=$NR_x$)$R_x$; —$NR_xC(O)R_x$, —$NR_xC(O)N(R_x)_2$, —$NR_xCO_2R_y$, —$NR_xC(O)C(O)R_y$, —$NR_xC(S)NH_2$, —$NR_xC(S)NHR_x$, —$NR_xC(NH)NH_2$, —$NR_xC(NH)NHR_x$, —$NR_xC(NH)R_x$, —C(NRx)$NHR_x$—S (O)$R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of disclosed compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ===== denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereoisomers of disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that the disclosure embraces both solvated and unsolvated forms of disclosed compounds. In one embodiment, a disclosed compound is amorphous or is a single polymorph. In another embodiment, a disclosed compound is a mixture of polymorphs. In another embodiment, a disclosed compound is in a crystalline form.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a disclosed compound may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the examples herein by substituting an isotopically labeled reagent for a non-isotopically labeled reagent.

In some embodiments one or more of the nitrogen atoms of a disclosed compound if present are oxidized to N-oxide.

An exemplary synthetic route for the preparation of a disclosed compound is shown in the schemes below. As will be understood by the skilled artisan, diastereomers can be separated from the reaction mixture using column chromatography.

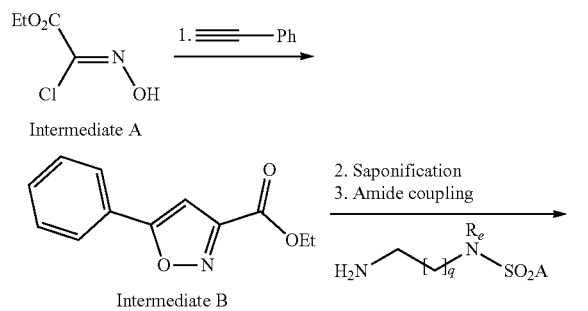

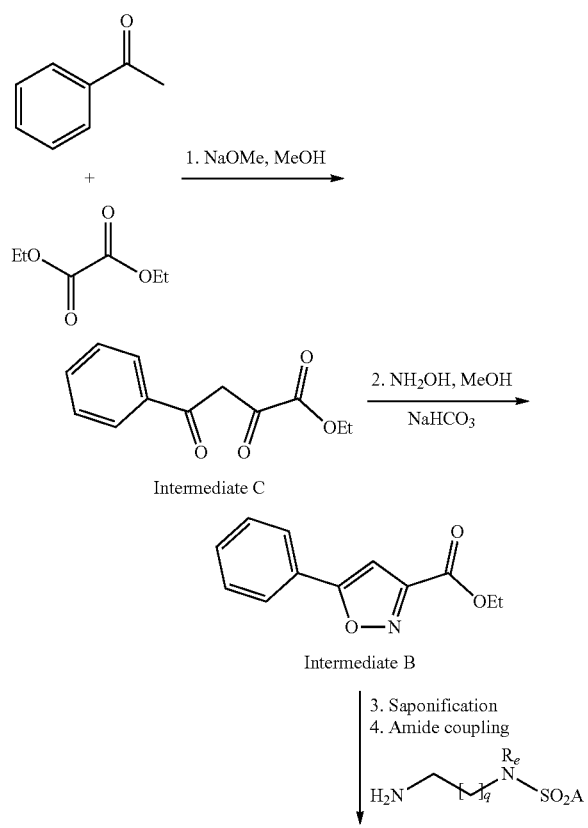

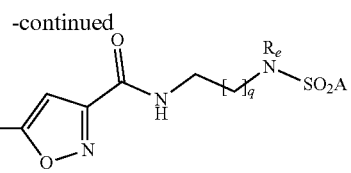

Disclosed compounds can also be prepared using methods described in the literature, including, but not limited to, *J. Med. Chem.* 2011, 54(13), 4350-64; *Russian Journal of Organic Chemistry*, 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, contemplated herein in an embodiment is a method of increasing CFTR activity in a subject comprising administering an effective amount of a disclosed compound. Also contemplated herein is a method of treating a patient suffering from a condition associated with CFTR activity comprising administering to said patient an effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X;

W1282X/N1303K, 591Δ18/E831X, F508del/R117H/N1303K/3849+10kbC>T; Δ303K/384; and DF508/G178R).

In certain embodiments, the mutation is a Class I mutation, e.g., a G542X Class I mutation; e.g., a Class II/I mutation, e.g., a ΔF508/G542X compound heterozygous mutation. In other embodiments, the mutation is a Class III mutation, e.g., a G551D Class III mutation; e.g., a Class II/Class III mutation, e.g., a ΔF508/G551D compound heterozygous mutation. In still other embodiments, the mutation is a Class V mutation, e.g., a A455E Class V mutation; e.g., a Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Using chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, a method of treating cystic fibrosis is contemplated, comprising administering an effective amount of a disclosed compound. Treatment of other conditions associated with CFTR activity, including conditions associated with deficient CFTR activity using disclosed compounds is also contemplated in certain embodiments.

In some embodiments, a method of treating a condition associated with deficient or decreased CFTR activity comprising administering an effective amount of a disclosed compound that enhances CFTR activity is provided. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, AP-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, a contemplated method of administering a disclosed compound includes administering at least one additional therapeutic agent, or administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), VX-809 (3-(6-(1-(2,2-difluorobenzo[d][1,3]dioxol-5-yl)cyclopropanecarbox-amido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG2222 (for example, a CFTR corrector); and compounds described in, e.g., WO2014/144860 and 2014/176553, hereby incorporated by reference. Non-limiting examples of modulators include QBW-251, QR-010, NB-124, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agent and incorporated by reference. Non-limiting examples of anti-inflammatory agents include N6022 (3-(5-(4-(1H-imidazol-1-yl) phenyl)-1-(4-carbamoyl-2-methyl-phenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983 and GLPG2222) or potentiator (e.g., ivacaftor, genistein and GLPG1837). In certain of these embodiments, one of the at least two additional therapeutic agents is a CFTR corrector (e.g., VX-809, VX-661 and VX-983) and the other is a CFTR potentiator (e.g., ivacaftor and genistein). In certain of these embodiments, one of the at least two additional therapeutic agents is a CFTR corrector (e.g., GLPG2222) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances read-through of stop codons (e.g., NB 124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, GLPG2222, NB 124, ataluren) and/or the other is a CFTR potentiator (e.g., ivacaftor, genistein, and GLPG1837); e.g., one of the at least two additional therapeutic agents is GLPG2222, and the other is GLPG1837; or one of the at least two additional therapeutic agents is VX-809 or VX-661, and the other is a ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1G > A Splice-site mutation in gene intron 16 |
| VI | Reduced due to protein instability | N287Y a A -> T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120 + 1 G > A | heterozygote | Unaffected |
| Δ508F/W1204X | compound heterozygote | pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, S549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g, ΔF508 mutation, as compared to administration of ivacaftor alone. Another combination therapy that includes a disclosed compound may also include an effective amount of a readthrough agent (e.g., ataluren, NB 124) and an effective amount of disclosed compound that may act as an amplifier.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g, VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

In an embodiment, contemplated methods may include for example, administering prodrugs of the compounds described herein, for example, prodrugs of a compound of Formula (Ia) or (Ib) or (II), or a pharmaceutical composition thereof or method of use of the prodrug.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a disclosed compound or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a disclosed compound contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino ($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

If a disclosed compound incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Also contemplated in certain embodiments is the use of clathrates of the compounds described herein, pharmaceutical compositions comprising the clathrates, and methods of use of the clathrates. Clathrates of a disclosed compound e.g., Formula (Ia) or (Ib) or (II), or a pharmaceutical composition thereof are also contemplated herein.

As discussed above, the disclosure provides for administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

In an embodiment, treatment of a condition associated with a dysfunction in proteostasis in a subject comprising administering to said subject an effective amount of a disclosed compound that enhances, improves or restores proteostasis of a protein is provided. Proteostasis refers to protein homeostasis. Dysfunction in protein homeostasis is a result of protein misfolding, protein aggregation, defective protein trafficking or protein degradation. For example, the disclosure encompasses administering a compound of Formula (Ia) or (Ib) that corrects protein misfolding, reduces protein aggregation, corrects or restores protein trafficking and/or affects protein degradation for the treatment of a condition associated with a dysfunction in proteostasis. In some aspects of the disclosure, a compound e.g., of Formula (Ia) or (Ib) that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucosaminidase, α-galactosidase A, cysteine transporter, acid ceramidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. The compounds of Formula (Ia) or (Ib) can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, Lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gml gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In yet additional embodiments, a disclosed method is directed to treating a disease associated with a dysfunction in proteostasis, wherein the disease affects the respiratory system or the pancreas. In certain additional embodiments, a disclosed method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. Contemplated herein are methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The disclosure additionally encompasses methods for treating hearing loss, such as noise-induced hearing loss, aminoglycoside-induced hearing loss, and cisplatin-induced hearing loss.

Additional conditions include those associated with a defect in protein trafficking and that can be treated according to disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The invention is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "intermediates" herein are contemplated as compounds of the invention.

Example 1: N-(3-((N-1-dimethyl-1H-imidazole)-2-sulfonamido)propyl)-5-phenylisoxazole-3-carboxamide

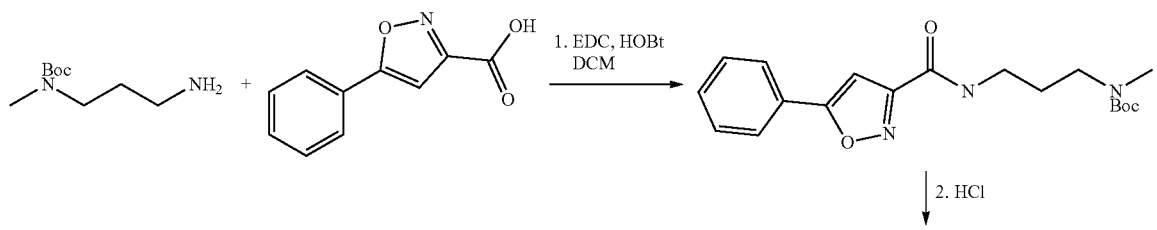

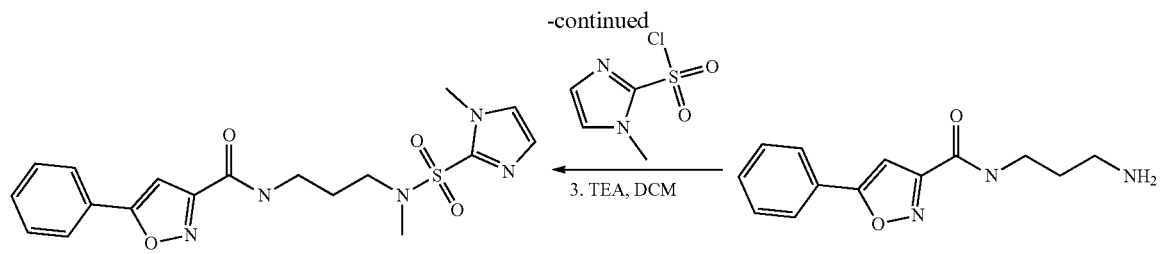

Step 1: Tert-butyl methyl(3-(5-phenylisoxazole-3-carboxamido)propyl)carbamate EDC.HCl (0.30 g, 0.0015 mol) was added to a solution of 5-phenylisoxazole-3-carboxylic acid (0.2 g, 0.0010 mol) and tert-butyl (3-aminopropyl)(methyl)carbamate (0.19 g, 0.0010 mol) in THF (4 mL) followed by addition HOBt (0.21 g, 0.0015 mol) at rt and reaction mixture was stirred at rt for 16 h. Progress the reaction was monitored by TLC. After completion, reaction was quenched with water (20 mL), extracted with ethyl acetate (2×25 mL), combined organic layer was dried over sodium sulfate and evaporated volatiles under vacuum. The crude was purified by column chromatography using 100-200 mesh silica eluted with 50% ethyl acetate in Hexane to give product (0.14 g, 36.74%) as a white solid. $^1$H NMR (400 MHz, CDCl$_3$): δ 7.79-7.77 (m, 2H), 7.47-7.46 (m, 3H), 6.94 (s, 1H), 3.44 (br, 2H), 3.35 (br, 2H), 2.85 (s, 3H), 1.79 (br, 2H), 1.46 (s, 9H), LC-MS: [M+H]$^+$ 360.1.

Step 2: N-(3-(methylamino)propyl)-5-phenylisoxazole-3-carboxamide a mixture of tert-butyl methyl(3-(5-phenylisoxazole-3-carboxamido)propyl)carbamate (0.19 g, 0.00052 mol) and HCl (5 mL) in diethyl ether was stirred under N$_2$ atmosphere at rt for 3 h. Reaction was monitored by TLC. After completion, volatiles were removed under vacuum to get 0.15 g of crude intermediate as an off-white solid which was carried forward to next step without purification.

Step 3: N-(3-((N,1-dimethyl-1H-imidazole)-2-sulfonamido)propyl)-5-phenylisoxazole-3-carboxamide triethylamine (0.15 mL, 0.115 g, 0.0011 mol) was added to a cold (0° C.) solution of N-(3-(methylamino)propyl)-5-phenylisoxazole-3-carboxamide (0.15 g, 0.0003 mol) in DCM (5 mL) and the mixture was stirred at rt for 15 min. Methylimidazole-2-sulfonyl chloride (0.075 g, 0.00041 mol) was added at 0° C. and the resulted reaction mixture was further stirred at rt for 1 h. Reaction was monitored by TLC. After completion, volatiles were removed under vacuum to dryness. The crude was purified by column chromatography using 100-200 mesh silica eluted with 80% ethyl acetate in hexane to give the product.

Yield: 48.8%
Appearance: white solid
Analytical data: $^1$H NMR (400 MHz, CDCl$_3$): δ 7.80-7.76 (m, 2H), 7.50-7.44 (m, 4H), 7.03-7.02 (d, 1H), 6.94-6.93 (d, 2H), 3.93 (s, 3H), 3.63-3.58 (q, 2H), 3.51-3.48 (t, 2H), 3.07 (s, 3H), 1.95-1.89 (m, 2H).
LC-MS [M+H]$^+$ 404.0.
HPLC: 98.25% at 254 nm and 97.98% at 220 nm.

Example 2: N-(3-(N-methyl-1H-imidazole-2-sulfonamido)propyl)-5-phenylisoxazole-3-carboxamide

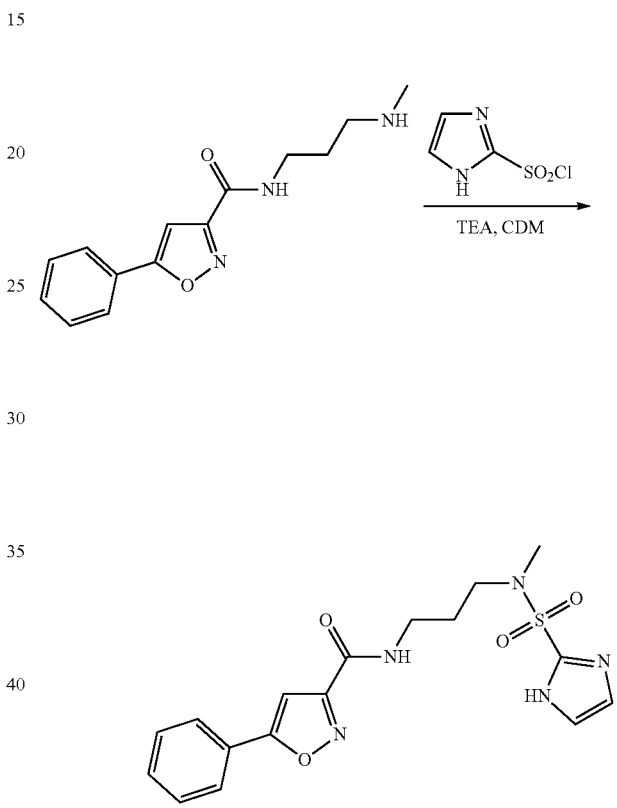

triethylamine (0.18 mL, 0.13 g, 0.0013 mol) was added to a cold (0° C.) solution of N-(3-(methylamino)propyl)-5-phenylisoxazole-3-carboxamide (0.2 g, 0.00067 mol) in DCM (5 mL) and the mixture was stirred at rt for 15 min. $^1$H-Imidazole-2-sulfonyl chloride hydrochloride (0.13 g, 0.00067 mol) was added to the mixture and then stirred at RT for 1 h. Reaction was monitored by TLC. After completion, volatiles were removed under vacuum to dryness. The crude was purified by column chromatography using 100-200 mesh silica, eluted with ethyl acetate to give the compound as a white solid.

Yield: 18.5%
Appearance: white solid
Analytical data: $^1$H NMR (400 MHz, DMSO d$_6$): δ 13.50 (br, 1H), 8.84-8.81 (t, 1H), 7.94-7.92 (m, 2H), 7.57-7.51 (m, 3H), 7.35 (s, 2H), 7.20 (br, 1H), 3.29-3.26 (m, 2H), 3.16-3.12 (t, 2H), 2.79 (s, 3H), 1.81-1.74 (m, 2H).
LC-MS: [M+H]$^+$ 390.2
HPLC: 99.64% at 200 nm and 99.62 at 220 nm.

Example 3: N-(3-((1-(methoxymethyl)-N-methyl-1H-imidazole)-2-sulfonamido)propyl)-5-phenylisoxazole-3-carboxamide

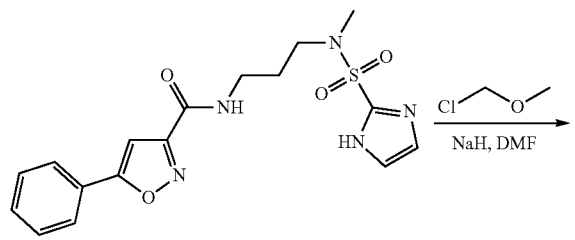

NaH (0.012 g, 0.308 mmol) was added to a cold solution (0° C.) of N-(3-(N-methyl-1H-imidazole-2-sulfonamido)propyl)-5-phenylisoxazole-3-carboxamide (0.1 g, 0.257 mmol) in DMF (2 mL) and the mixture was stirred at rt for 1 h. Methoxymethyl chloride (0.030 g, 0.385 mmol) was added at 0° C. and the reaction mixture was stirred at RT for 1 h. Reaction was monitored by TLC. After completion, water was added and extracted with ethyl acetate (3×20 ml), washed with brine and evaporated volatiles under vacuum to dryness. The crude was purified by Prep HPLC to afford the product (0.030 g).

Yield: 27.3%.

Appearance: white solid.

Analytical data: $^1$H NMR (400 MHz, CDCl$_3$): δ 7.78-7.76 (m, 2H), 7.50-7.42 (m, 4H), 7.17-7.16 (d, 1H), 7.110-7.113 (d, 1H), 6.93 (s, 1H), 5.6 (s, 1H), 3.61-3.59 (m, 2H), 3.50-3.47 (t, 2H), 3.38-3.35 (d, 3H), 3.07 (s, 3H), 1.96-1.89 (m, 2H).

LC-MS: [M+H]$^+$ 433.7

HPLC: 99.87% at 257 nm and 99.86 at 220 nm.

Example 4: N-(2-((3-(hydroxymethyl)-1H-pyrazole)-5-sulfonamido)ethyl)-5-phenylisoxazole-3-carboxamide

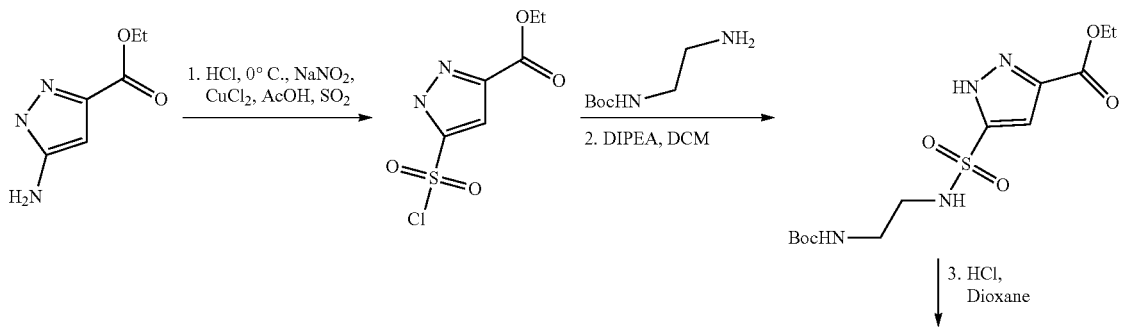

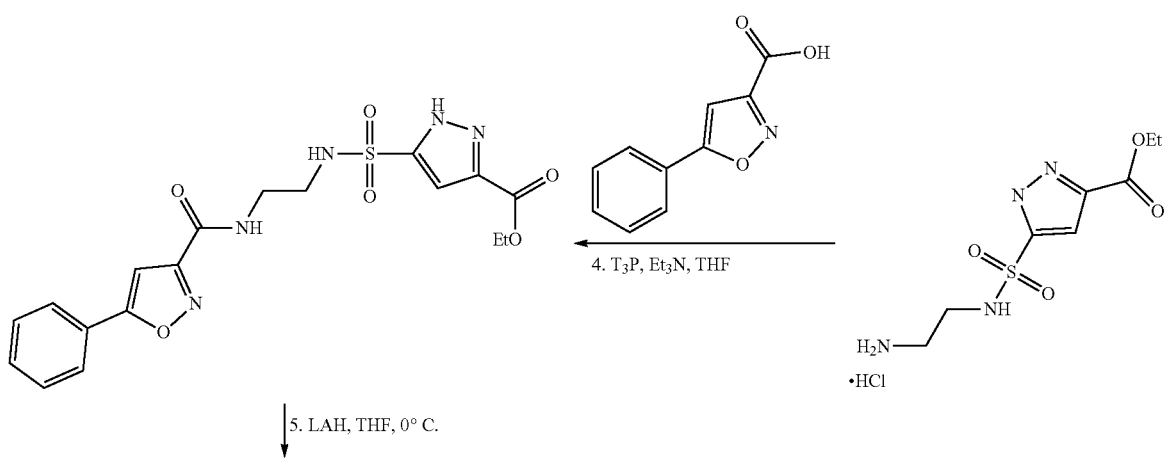

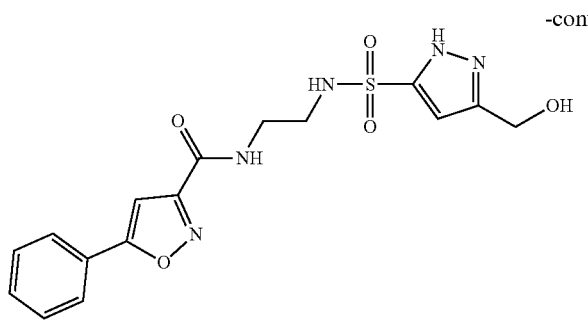

Step-1: ethyl 5-(chlorosulfonyl)-1H-pyrazole-3-carboxylate a solution of $NaNO_2$ (0.94 g, 0.014 mol) in water (4 mL) was added drop wise was added slowly to a cold (0° C.) suspension of ethyl 5-amino-1H-pyrazole-3-carboxylate (2 g, 0.0129 mol) in 6N HCl (8 mL) keeping the temperature below 5° C. The resultant reaction mixture was stirred at 5-10° C. for 1 h. A solution of $SO_2$ was prepared by bubbling the gas into AcOH (12.8 mL) until the solution gained at least 0.8 g in weight and then a solution of $CuCl_2$ (0.69 g, 0.0051 mol) in 3 mL of water was added and stirred for 10 minutes. Then the diazotized solution was added to $SO_2$ gas solution at room temperature and stirred at room temperature for 20 minutes. The reaction mixture was diluted with water and extracted with diethyl ether (20 mL×2). Combined organic layers were washed with water, brine, dried over $Na_2SO_4$ and concentrated under reduced pressure to afford crude product (1.2 g, 40%) as off white solid. The crude off-white solid was directly used for next step without purification. $^1H$ NMR (400 MHz, $CDCl_3$): δ 11.69 (br, 1H), 7.38 (s, 1H), 4.45 (q, J=7.1 Hz, 2H), 1.42 (t, J=7.1 Hz, 3H); LC-MS: [M−H]$^-$=236.9 m/z.

Step-2: ethyl 5-(N-(2-((tert-butoxycarbonyl)amino) ethyl)sulfamoyl)-1H-pyrazole-3-carboxylate DIEPA (1.5 mL, 0.0085 mol) was added to a cold (0° C.) solution of tert-butyl (2-aminoethyl)carbamate (1 g, 0.00420 mol) in 20 ml of DCM followed by addition of ethyl 5-(chlorosulfonyl)-1H-pyrazole-3-carboxylate (1 mL, 0.0063 mol). The resultant reaction mixture was stirred at room temperature for 5 h after which it was poured onto ice-water and extracted with DCM (2×10 mL). Combined organic layers were washed with water, brine, dried over $Na_2SO_4$, concentrated under reduced pressure to obtain crude product. The crude was purified by column chromatography on silica gel (100-200 mesh) using 5% methanol in DCM to afford the product (0.6 g, 40%) as off-white solid. $^1H$ NMR (400 MHz, $CDCl_3$): δ 7.21 (s, 1H), 6.34 (br, 1H), 4.99 (br, 1H), 4.40 (q, J=7.1 Hz, 2H), 3.28-3.18 (m, 4H), 1.42 (s, 9H), 1.39 (t, J=7.1 Hz, 3H); LC-MS: [M−H]$^-$=361.0 m/z.

Step-3: ethyl 5-(N-(2-aminoethyl)sulfamoyl)-1H-pyrazole-3-carboxylate

4N HCl in dioxane (30 mL) was added drop wise to a cold solution at 0° C. of ethyl 5-(N-(2-((tert-butoxycarbonyl) amino)ethyl)sulfamoyl)-1H-pyrazole-3-carboxylate (0.6 g, 0.00165 mol) in 5 mL of 1, 4-dioxane. The resultant reaction mixture was stirred at room temperature for 3 h. Volatiles were removed under vacuum to yield the hydrochloride salt (0.5 g, crude) as sticky mass. The crude was directly used in the next reaction. $^1H$ NMR (400 MHz, DMSO-$d_6$): δ 14.91 (br, 1H), 8.15 (br, 1H), 7.98 (br, 3H), 7.14 (s, 1H), 4.34 (q, J=7.1 Hz, 2H), 3.14-3.09 (m, 2H), 2.89-2.85 (m, 2H), 1.31 (t, J=7.1 Hz, 3H); LC-MS: [M+H]$^+$=263.0 m/z.

Step-4: ethyl 5-(N-(2-(5-phenylisoxazole-3-carboxamido)ethyl)sulfamoyl)-1H-pyrazole-3-carboxylate a suspension of ethyl 5-(N-(2-aminoethyl)sulfamoyl)-1H-pyrazole-3-carboxylate (0.5 g), 5-phenylisoxazole-3-carboxylic acid (0.43 g, 0.00229 mol), $Et_3N$ (0.8 mL, 0.0057 mol) and $T_3P$ (1.8 g, 0.0057 mol) in 15 mL of anhydrous THF was stirred at room temperature. The reaction mixture was stirred at room temperature for 6 h. Volatiles were removed under vacuum and the crude was dissolved in ethyl acetate (20 mL). The organic layer was washed with saturated $Na_2CO_3$ solution (10 mL×2), water, brine, dried over $Na_2SO_4$ and concentrated under vacuum to obtain a residue which was purified by column chromatography on silica gel (100-200 mesh) using 5% methanol in DCM to afford product (0.250 g, 35% from step 2) as off-white solid. $^1H$ NMR (400 MHz, $CDCl_3$+2drops DMSO-$d_6$): δ 7.88 (br, 1H), 7.77-7.75 (m, 2H), 7.46-7.45 (m, 3H), 7.13 (s, 1H), 6.91 (s, 1H), 6.65 (br, 1H), 4.30 (q, J=7.1 Hz, 2H), 3.59-3.55 (m, 2H), 3.35-3.31 (m, 2H), 1.32 (t, J=7.1 Hz, 3H); LC-MS: [M+H]$^+$=434.2 m/z.

Step-5: N-(2-((3-(hydroxymethyl)-1H-pyrazole)-5-sulfonamido)ethyl)-5-phenylisoxazole-3-carboxamide to a stirred suspension of $LiAlH_4$ (0.180 g, 0.000472 mol) in 10 mL of anhydrous THF was added a solution of ethyl 5-(N-(2-(5-phenylisoxazole-3-carboxamido)ethyl)sulfamoyl)-1H-pyrazole-3-carboxylate (0.4 g, 0.00094 mol) in 4 mL of THF at 0° C. and stirred at 0° C. for 2 h. The reaction mixture was quenched slowly with saturated solution of $NH_4Cl$ (5 mL) and the resulting solid suspension was stirred for 10 minutes, filtered through celite, washed with ethyl acetate (10 mL). The combined filtrate was washed with water, brine, dried over $Na_2SO_4$, filtered and concentrated under reduced pressure to obtain crude compound. The crude was purified by column chromatography on silica gel (100-200 mesh) using 5% methanol in DCM to yield product (0.1 g).

Yield: 28%
Appearance: off-white solid
Analytical data: $^1H$ NMR (400 MHz, $CD_3OD$): δ 7.89-7.86 (m, 2H), 7.54-7.50 (m, 3H), 7.07 (s, 1H), 6.61 (s, 1H), 4.62 (s, 2H), 3.50 (t, J=6.2 Hz, 2H), 3.24 (t, J=6.2 Hz, 2H).

LC-MS: [M+H]$^+$=392.2 m/z

HPLC Purity: 91.71% at 220 nm and 95.64% at 254 nm.

Example 5: N-(3-((3-(hydroxymethyl)-1H-pyrazole)-5-sulfonamido)propyl)-5-phenylisoxazole-3-carboxamide

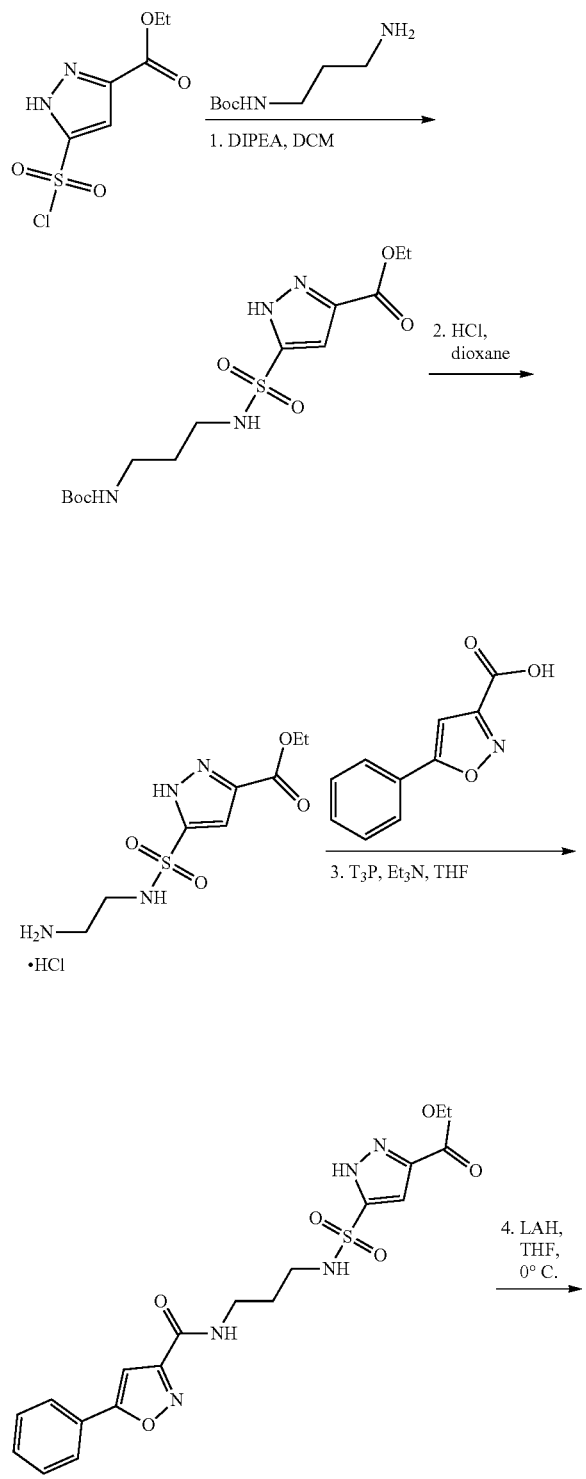

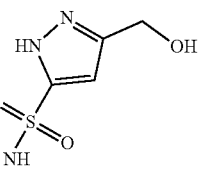

Step-1: ethyl 5-(N-(3-((tert-butoxycarbonyl)amino)propyl)sulfamoyl)-1H-pyrazole-3-carboxylate DIEPA (1.5 mL, 0.0085 mol) was added to a cold (0° C.) solution of ethyl 5-(chlorosulfonyl)-1H-pyrazole-3-carboxylate (1 g, 0.00420 mol) in 20 ml of DCM followed by addition of tert-butyl (3-aminopropyl)carbamate (1.1 g, 0.0063 mol). The resultant reaction mixture was stirred at room temperature for 5 h before pouring onto ice-water (20 mL) and extracting with DCM (2×20 mL). Combined organic layers were washed with water, brine, dried over $Na_2SO_4$ and concentrated under reduced pressure to obtain crude product. The crude was purified by column chromatography on silica gel (100-200 mesh) using 5% methanol in DCM to afford product (0.6 g, 37%) as an off-white solid. $^1$H NMR (400 MHz, CDCl$_3$): δ 7.21 (s, 1H), 6.07 (br, 1H), 4.74 (br, 1H), 4.40 (q, J=7.1 Hz, 2H), 3.21 (q, J=6.0 Hz, 2H), 3.15-3.10 (m, 2H), 1.68-1.66 (m, 2H), 1.44-1.39 (12H); LC-MS: [M–H]$^+$=375.1 m/z.

Step-2: ethyl 5-(N-(3-aminopropyl)sulfamoyl)-1H-pyrazole-3-carboxylate a solution of HCl (4N) in dioxane (30 mL) was added dropwise to a cold (0° C.) solution of ethyl 5-(N-(3-((tert-butoxycarbonyl)amino)propyl)sulfamoyl)-1H-pyrazole-3-carboxylate (0.6 g, 0.0016 mol) in 1,4-dioxane (6 mL) and stirred at room temperature for 3 h. Volatiles were removed under vacuum to obtain crude hydrochloride salt (0.6 g crude) which was directly used the next reaction. $^1$H NMR (400 MHz, DMSO-d$_6$): δ 14.83 (br, 1H), 7.96 (br, 1H), 7.85 (br, 3H), 7.1 (s, 1H), 4.36-4.31 (q, J=7.0 Hz, 2H), 2.96-2.91 (q, J=6.7 Hz, 2H), 2.80-2.75 (m, 2H), 1.74-1.68 (m, 2H), 1.31 (t, J=7.0 Hz, 3H); LC-MS: [M+H]$^+$=277.2 m/z.

Step-3: ethyl 5-(N-(3-(5-phenylisoxazole-3-carboxamido)propyl)sulfamoyl)-1H-pyrazole-3-carboxylate a suspension of ethyl 5-(N-(3-aminopropyl)sulfamoyl)-1H-pyrazole-3-carboxylate (0.6 g), 5-phenylisoxazole-3-carboxylic acid (0.493 g, 0.0026 mol), Et$_3$N (1.1 mL, 0.0065 mol) and T$_3$P (2 g, 0.0065 mol) in anhydrous THF (20 mL) was stirred at room temperature for 6 h. Volatiles were removed under reduced pressure and the residue was dissolved in ethyl acetate (20 mL). The organic layer was washed with saturated Na$_2$CO$_3$ solution (10 mL×2), water, brine, dried over Na$_2$SO$_4$ and concentrated under reduced pressure to afford obtain crude compound. The crude was purified by column chromatography on silica gel (100-200 mesh) using 5% methanol in DCM to give product (0.450 g, 63%) as off-white solid. $^1$H NMR (400 MHz, CDCl$_3$): δ 11.91 (br, 1H), 7.79-7.77 (m, 2H), 7.50-7.46 (m, 3H), 7.37 (m, 1H), 7.24 (s, 1H), 6.98 (s, 1H), 4.41-4.36 (q, J=7.1 Hz, 2H), 3.62-3.57 (m, 2H), 3.26-21 (m, 2H), 1.89-1.84 (m, 2H), 1.37 (t, J=7.1 Hz, 3H); LC-MS: [M+H]$^+$=448.0 m/z.

Step-4: N-(3-((3-(hydroxymethyl)-1H-pyrazole)-5-sulfonamido)propyl)-5-phenylisoxazole-3-carboxamide a THF (5 mL) solution of ethyl 5-(N-(3-(5-phenylisoxazole-3-carboxamido)propyl)sulfamoyl)-1H-pyrazole-3-carboxylate was added slowly to a cold (0° C.) suspension of LiAlH$_4$ (0.191 g, 0.00503 mol) in anhydrous THF (10 mL) and the reaction mixture was stirred at 0° C. for 2 h. The reaction mixture was quenched slowly with a saturated solution of NH$_4$Cl (5 mL), and the resulting solid suspension was stirred for 10 minutes, filtered through celite and washed with ethyl acetate (10 mL). Combined filtrate was washed with water, brine, dried over Na$_2$SO$_4$, filtered and concentrated under reduced pressure to obtain crude compound. The crude was purified by column chromatography on silica gel (100-200 mesh) using 5% methanol in DCM to obtain product (0.085 g).

Yield: 21%.

Appearance: off-white solid.

Analytical data: $^1$H NMR (400 MHz, CD$_3$OD): δ 7.88-7.86 (m, 2H), 7.55-7.50 (m, 3H), 7.07 (s, 1H), 6.61 (s, 1H), 4.64 (s, 2H), 3.45-3.42 (t, J=6.8 Hz, 2H), 3.09-3.05 (t, J=6.8 Hz, 2H), 1.84-1.77 (m, 2H).

LC-MS: [M+H]$^+$=406.0 m/z.

HPLC Purity: 96.04% at 220 nm and 95.52% at 254 nm.

Example 6: 5-phenyl-N-(3-(pyrimidine-2-sulfonamido)propyl)isoxazole-3-carboxamide

Step 1a: Pyrimidine-2-Sulfonyl Chloride a solution of pyrimidine-2-thiol (800 mg, 7.13 mmol, 1.00 eq.) in dichloromethane (10 mL) was added dropwise-to a 5° C. solution of sodium hypochlorite (16 mL) and conc. hydrogen chloride aqueous (20 mL) in dichloromethane (10 mL). The resulting solution was stirred for 15 min at −5° C. in an ice/salt bath. The resulting solution was extracted with dichloromethane (50 mL×3) and the combined organic layers were dried over anhydrous sodium sulfate and concentrated under vacuum. This resulted in 600 mg (crude) of pyrimidine-2-sulfonyl chloride as a white solid.

Step 2a: pentafluorophenyl pyrimidine-2-sulfonate a solution of pyrimidine-2-sulfonyl chloride (300 mg, 1.68 mmol, 1.00 eq.) in dichloromethane (10 mL) was added slowly to a 0° C. solution of pentafluorophenol (310 mg, 1.68 mmol, 1.00 eq.) and TEA (510 mg, 5.04 mmol, 3.00 eq.) in dichloromethane (10 mL). The resulting solution was stirred for 1 hour at 0° C. in an ice/salt bath. The resulting mixture was concentrated under vacuum. The residue was applied onto a silica gel column with ethyl acetate/petroleum ether (1:10). This resulted in 230 mg (42%) of pentafluorophenyl pyrimidine-2-sulfonate as a white solid. LC-MS: [M+H]$^+$=327.

Step 1: tert-butyl N-[3-[(5-phenyl-1,2-oxazol-3-yl)formamido]propyl]carbamate tert-butyl N-(3-aminopropyl)carbamate (884 mg, 5.07 mmol, 1.20 eq.), HATU (1930 mg, 5.08 mmol, 1.20 eq.) were added to a solution of 5-phenyl-1,2-oxazole-3-carboxylic acid (800 mg, 4.23 mmol, 1.00 eq.) in dichloromethane (50 mL). DIEA (1638 mg, 12.67 mmol, 3.00 eq.) was added dropwise to the reaction mixture and then it was stirred for 2 hours at room temperature. The reaction was then

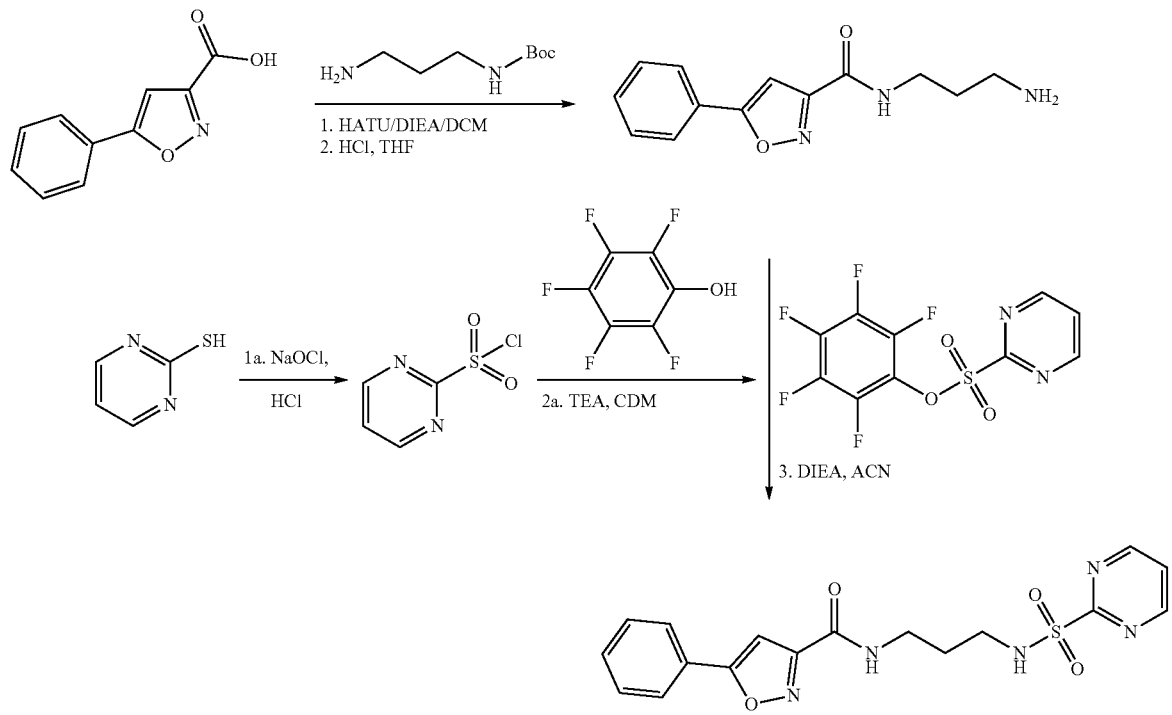

quenched by the addition of water, extracted with dichloromethane (3×50 mL) and the combined organic layers were dried over anhydrous sodium sulfate and concentrated under vacuum. The residue was applied onto a silica gel column with dichloromethane/methanol (100:1) to give 600 mg (41%) of tert-butyl N-[3-[(5-phenyl-1,2-oxazol-3-yl)formamido]propyl]carbamate as a white solid. LC-MS: [M+H]⁺=346.

Step 2: N-(3-aminopropyl)-5-phenyl-1,2-oxazole-3-carboxamide hydrochloride a solution of tert-butyl N-[3-[(5-phenyl-1,2-oxazol-3-yl)formamido]propyl]carbamate (800 mg, 2.32 mmol, 1.00 eq.) in tetrahydrofuran (15 mL) and conc. hydrogen chloride aqueous (2 mL) was stirred for 1 hour at room temperature. The resulting mixture was concentrated under vacuum. This resulted in 500 mg (88%) of N-(3-aminopropyl)-5-phenyl-1,2-oxazole-3-carboxamide hydrogen chloride as a white solid. LC-MS: [M+H]⁺=246.

Step 3: 5-phenyl-N-[3-(pyrimidine-2-sulfonamido)propyl]-1,2-oxazole-3-carboxamide DIEA (500 mg, 3.87 mmol, 3.00 eq.) was added dropwise to a solution of pentafluorophenyl pyrimidine-2-sulfonate (400 mg, 1.23 mmol, 1.00 eq.), N-(3-aminopropyl)-5-phenyl-1,2-oxazole-3-carboxamide (300 mg, 1.22 mmol, 1.00 eq.) and in acetonitrile (10 mL). The reaction mixture was stirred for 2 hours at room temperature and then concentrated under vacuum. The residue was applied onto a silica gel column with dichloromethane/methanol (50:1). The crude product (400 mg) was purified by Prep-HPLC with the following conditions (Waters): Column, XBridge™ Prep C18 5 um OBD™ 19*100 mm; mobile phase, water with 0.05% NH₄HCO₃ and CH₃CN (30.0% CH₃CN up to 65.0% in 10 min, up to 95.0% in 1.5 mn, down to 30.0% in 1.5 min); Detector, UV 254 nm. This resulted in 179 mg (38%) of 5-phenyl-N-[3-(pyrimidine-2-sulfonamido)propyl]-1,2-oxazole-3-carboxamide as a white solid.

LC-MS: [M+H]⁺=388

Analytical data: ¹H NMR (300 MHz, DMSO-d₆): δ 9.04-9.03 (d, J=4.8 Hz, 2H), 8.82-8.76 (m, 1H), 8.09-8.06 (m, 1H), 7.95-7.92 (m, 2H), 7.80-7.76 (m, 1H), 7.57-7.55 (m, 3H), 7.35 (s, 1H), 3.32-3.26 (m, 2H), 3.16-3.07 (m, 2H), 1.74-1.70 (m, 2H).

HPLC purity: 99.4% at 254 nm.

Example 7: 5-phenyl-N-(3-(pyridine-2-sulfonamido)propyl)isoxazole-3-carboxamide

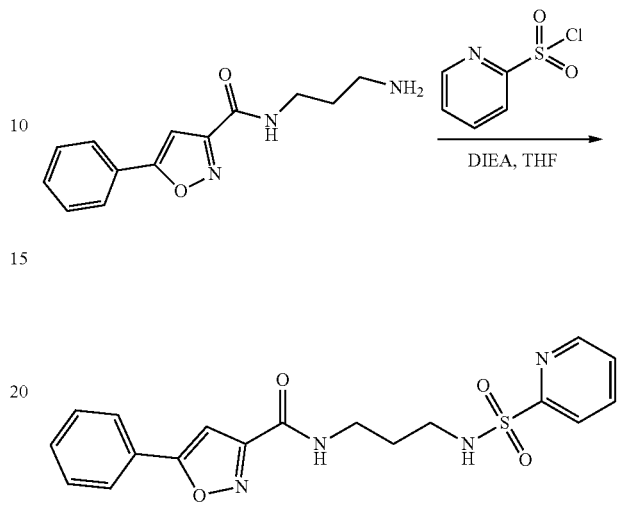

Pyridine-2-sulfonyl chloride (172 mg, 0.97 mmol, 1.00 eq.) was added dropwise to a 0° C. solution of N-(3-aminopropyl)-5-phenyl-1,2-oxazole-3-carboxamide (240 mg, 0.98 mmol, 1.00 eq.) and DIEA (379 mg, 2.94 mmol, 3.00 eq.) in tetrahydrofuran (10 mL). The reaction mixture was stirred for 2 hours at 0° C., it was then concentrated under vacuum and the residue was purified by preparative TLC (dichloromethane/methanol=50:1). The resulting crude product was applied onto a silica gel column and eluted with dichloromethane/methanol (100:1-50:1) to give 240 mg (63%) of 5-phenyl-N-[3-(pyridine-2-sulfonamido)propyl]-1,2-oxazole-3-carboxamide as a white solid.

LC-MS: [M+H]⁺=387.

Analytical data: ¹H NMR: (300 MHz, DMSO-d₆): δ 8.79-8.74 (m, 2H), 8.10-8.05 (m, 1H), 7.94-7.85 (m, 4H), 7.68-7.64 (m, 1H), 7.58-7.54 (m, 1H), 7.34 (s, 1H), 3.29-3.22 (m, 2H), 3.01-2.94 (m, 2H), 1.69-1.61 (m, 2H).

HPLC purity: 98.6% at 254 nm.

Example 8: N-(2-((5-amino-3-(hydroxymethyl)-1H-pyrazol-1-yl)sulfonyl)ethyl)-5-phenylisoxazole-3-carboxamide

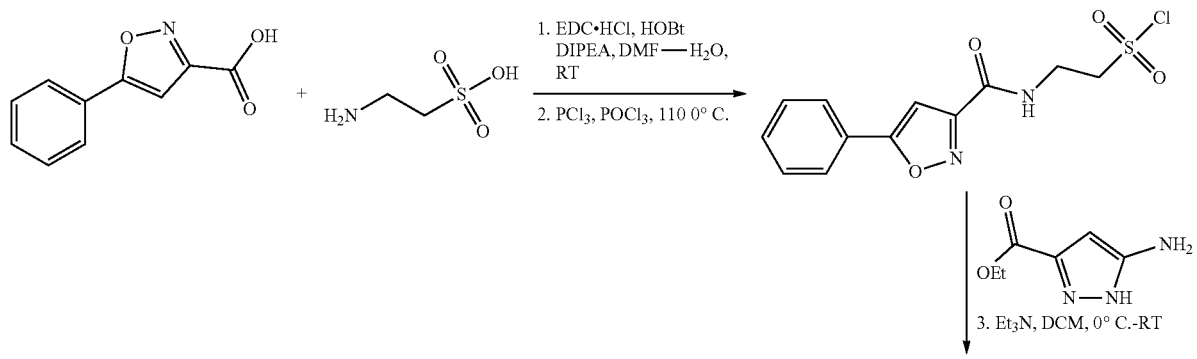

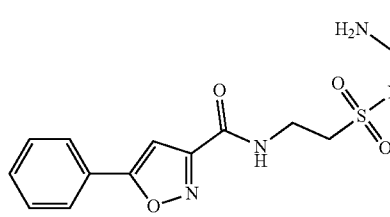
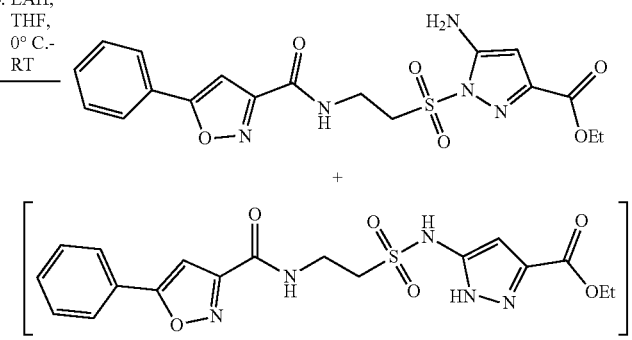

Step 1: 2-(5-phenylisoxazole-3-carboxamido)ethane-1-sulfonic acid

HOBt (2.56 g, 0.019 mol) was added to a solution of 2-aminoethane-1-sulfonic acid (2.97 g, 0.024 mol) and 5-phenylisoxazole-3-carboxylic acid (3.0 g, 0.016 mol) in DMF (150 mL) and water (25 mL), followed by EDC.HCl (4.54 g, 0.024 mol). Then DIPEA (6.12 g, 0.047 mol) was added drop wise to the reaction mixture and stirred at room temperature for 72 h. Volatiles were removed under reduced pressure to afford crude compound, which was further purified by preparative HPLC to obtain the product (500 mg, 10%) as off white solid. $^1$H NMR (400 MHz, D$_2$O): δ 7.81-7.79 (m, 2H), 7.52-7.51 (m, 3H), 6.94 (s, 1H), 3.73 (t, J=6.9 Hz, 2H), 3.17 (t, J=6.8 Hz, 2H), LC-MS: [M–H]$^-$=295.1.

Step 2: 2-(5-phenylisoxazole-3-carboxamido)ethane-1-sulfonyl chloride

PCl$_5$ (0.42 g, 0.002 mol) was added to an ice cooled suspension of 2-(5-phenylisoxazole-3-carboxamido)ethane-1-sulfonic acid (0.4 g, 0.001 mol) in POCl$_3$ (10 mL) and the resulting reaction mixture was heated to 110° C. for 12 h. The reaction mixture was cooled to room temperature and poured onto ice water. The precipitate thus obtained was filtered, washed with water and dried to obtain the product (300 mg, 71%) as a pale brown solid which was used as such for next step without further purification. $^1$H NMR (400 MHz, DMSO-d$_6$): 8.79-8.76 (m, 1H), 7.94-7.92 (m, 2H), 7.57-7.53 (m, 3H), 7.37 (s, 1H), 3.56-3.51 (m, 2H), 2.67 (t, J=7.0 Hz, 2H); LC-MS: [M–H]$^-$=313.2.

Step 3: ethyl 5-amino-1-((2-(5-phenylisoxazole-3-carboxamido)ethyl)sulfonyl)-1H-pyrazole-3-carboxylate ethyl 5-amino-1H-pyrazole-3-carboxylate (124 mg, 0.794 mol) was added to a cold solution of 2-(5-phenylisoxazole-3-carboxamido)ethane-1-sulfonyl chloride (250 mg, 0.794 mmol) in DCM (20 mL) followed by addition of Et$_3$N (160 mg, 1.589 mmol) and the resulting reaction mixture was stirred at room temperature for 2 h. Volatiles were removed under reduced pressure to obtain crude compound which was chromatographed on silica gel (mesh 100-200) using 50% EtOAc in hexane as eluent to obtain mixture of isomeric products (120 mg, crude) as off white sticky solid. LC-MS: [M+H]$^+$=434.1.

Step 4: N-(2-((5-amino-3-(hydroxymethyl)-1H-pyrazol-1-yl)sulfonyl)ethyl)-5-phenylisoxazole-3-carboxamide LAH (20 mg, 0.51 mmol) was added to an ice cooled solution of ethyl 5-amino-1-((2-(5-phenylisoxazole-3-carboxamido)ethyl)sulfonyl)-1H-pyrazole-3-carboxylate (100 mg, 0.2537 mmol) in THF (10 mL) and the reaction mixture was stirred for 1 h at the same temperature. Then the reaction mixture was quenched with saturated NH$_4$Cl solution and filtered through celite pad. The filtrate was dried over anhydrous sodium sulfate and concentrated under reduced pressure to afford crude compound which was further purified by preparative HPLC to obtain N-(2-((5-amino-3-(hydroxymethyl)-1H-pyrazol-1-yl)sulfonyl)ethyl)-5-phenylisoxazole-3-carboxamide (23 mg, 7% over two steps).

Appearance: white solid

Analytical data: $^1$H NMR (400 MHz, DMSO-d$_6$): δ 8.89-8.87 (m, 1H), 7.94-7.92 (m, 2H), 7.58-7.54 (m, 3H), 7.36 (s, 1H), 6.07 (s, D$_2$O exchangeable, 2H), 5.34 (s, 1H), 5.16 (t, J=6.0 Hz, 1H), 4.25 (d, J=6.0 Hz, 2H), 3.76 (t, J=6.6 Hz, 2H), 3.61-3.56 (m, 2H).

LC-MS: [M+H]$^+$=391.9

HPLC Purity: 98.50% at 254 nm and 98.37% at 220 nm.

Example 9: (S)—N-(2-(N-(5-(1-hydroxyethyl)-1,3,4-thiadiazol-2-yl)sulfamoyl)ethyl)-5-phenylisoxazole-3-carboxamide and (R)—N-(2-(N-(5-(1-hydroxyethyl)-1,3,4-thiadiazol-2-yl)sulfamoyl)ethyl)-5-phenylisoxazole-3-carboxamide

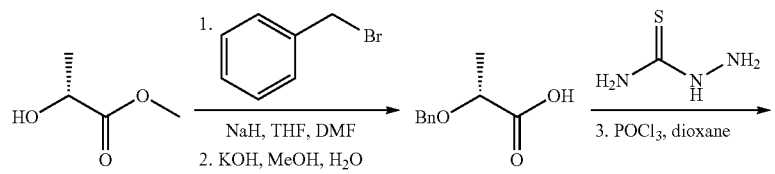

-continued

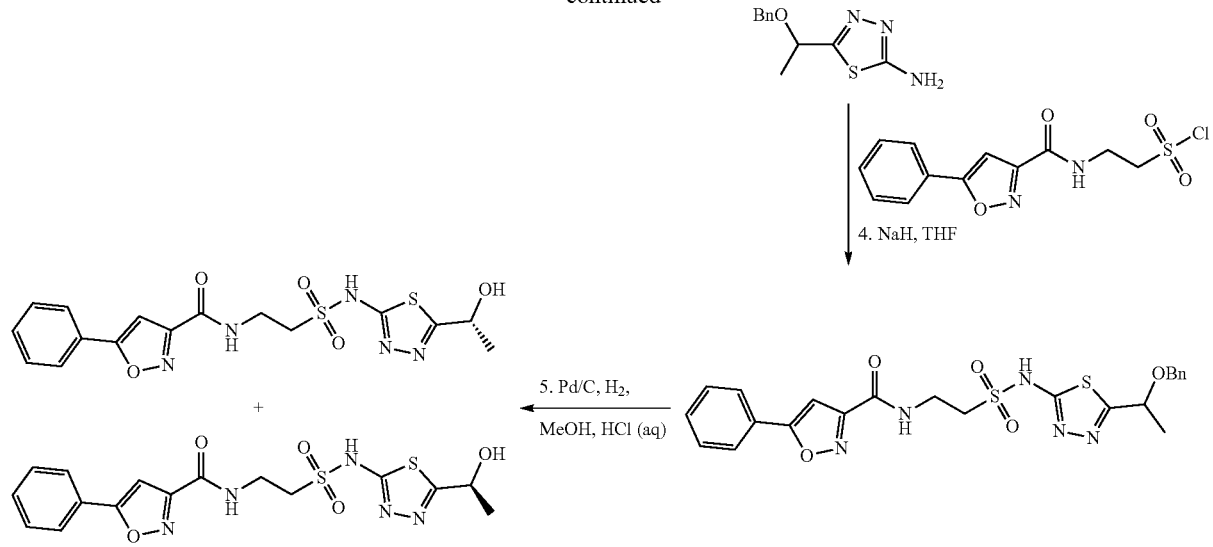

Step 1: methyl (2R)-2-(benzyloxy)propanoate sodium hydride (3.7 g, 154.17 mmol, 1.20 eq.) was added to a solution of methyl (2R)-2-hydroxypropanoate (8 g, 76.85 mmol, 1.00 eq.) in DMF (100 mL) and tetrahydrofuran (100 mL) followed by addition of (bromomethyl) benzene (14.4 g, 84.19 mmol, 1.10 eq.). The resulting solution was stirred for 16 hours at 75° C., the reaction was then quenched with water. The resulting solution was extracted with ethyl acetate and the organic combined layer was washed with brine, dried over anhydrous sodium sulfate and concentrated under vacuum. The residue was applied onto a silica gel column with ethyl acetate/petroleum ether (1:10). This resulted in 12 g (80%) of methyl (2R)-2-(benzyloxy)propanoate as yellow oil.

Step 2: (2R)-2-(benzyloxy)propanoic acid

KOH (9.2 g, 163.96 mmol, 3.00 eq.) was added to a solution of methyl (2R)-2-(benzyloxy)propanoate (11 g, 56.63 mmol, 1.00 eq.) in methanol/water (90 mL/10 mL and the solution was stirred for 30 minutes at room temperature. The reaction was concentrate and then diluted with water. The resulting solution was washed with of ethyl acetate. The pH value of the resulting aqueous layer was adjusted to 5 with hydrogen chloride aqueous (2 mol/L). The resulting solution was extracted with ethyl acetate and the combined organic layer was washed with brine, dried over anhydrous sodium sulfate and concentrated under vacuum to give 9.6 g (94%) of (2R)-2-(benzyloxy)propanoic acid as colorless oil. LC-MS: [M+H]$^+$=179.

Step 3: 5-[1-(benzyloxy)ethyl]-1,3,4-thiadiazol-2-amine

POCl$_3$ (4.0 g, 26.09 mmol, 1.00 eq.) was added dropwise to a 80° C. solution of (2S)-2-(benzyloxy)propanoic acid (4.7 g, 26.08 mmol, 1.00 eq.) and aminothiourea (2.4 g, 26.33 mmol, 1.00 eq.) in dioxane (100 mL). The resulting solution was stirred for 2 hours at 80° C., and it was then quenched by the addition of ice-water. The pH value of the solution was adjusted to 8 with saturated sodium bicarbonate aqueous. The solids were collected by filtration to give 4 g (65%) of 5-[1-(benzyloxy)ethyl]-1,3,4-thiadiazol-2-amine as a yellow solid. LC-MS: [M+H]$^+$=236.

Step 4: N-[2-([5-[1-(benzyloxy)ethyl]-1,3,4-thiadiazol-2-yl]sulfamoyl)ethyl]-5-phenyl-1,2-oxazole-3-carboxamide NaH (250 mg, 9.58 mmol, 1.50 eq.) was added to a solution of 5-[1-(benzyloxy)ethyl]-1,3,4-thiadiazol-2-amine (1 g, 4.25 mmol, 1.00 eq.) in tetrahydrofuran (80 mL) and the reaction was stirred for 1 hour at room temperature. 2-[(5-phenyl-1,2-oxazol-3-yl)formamido]ethane-1-sulfonyl chloride (1.4 g, 4.45 mmol, 1.00 eq.) was then added and the mixture was stirred for 15 min at room temperature. The reaction was then quenched by the addition of water, extracted with ethyl acetate and the organic layers combined. The resulting mixture was washed with brine, dried and concentrated under vacuum. The residue was applied onto a silica gel column with dichloromethane/methanol (20:1) to give 780 mg (36%) of N-[2-([5-[1-(benzyloxy) ethyl]-1,3,4-thiadiazol-2-yl]sulfamoyl)ethyl]-5-phenyl-1,2-oxazole-3-carboxamide as a white solid. LC-MS: [M+H]$^+$=514.

Step 5: N-(2-[[5-(1-hydroxyethyl)-1,3,4-thiadiazol-2-yl]sulfamoyl]ethyl)-5-phenyl-1,2-oxazole-3-carboxamide concentrated hydrogen chloride (0.2 mL) and Palladium carbon (40 mg) were added to a solution of N-[2-([5-[1-(benzyloxy)ethyl]-1,3,4-thiadiazol-2-yl]sulfamoyl)ethyl]-5-phenyl-1,2-oxazole-3-carboxamide (400 mg, 0.78 mmol, 1.00 eq.) in methanol (20 mL). To resulting solution was degassed and back filled with hydrogen gas and the resulting solution was stirred for 16 hours at 60° C. The solids were filtered out and the solvent was concentrated under vacuum. The residue was applied onto a silica gel column with ethyl acetate/petroleum ether (1:6) to give 55 mg (17%) of N-(2-[[5-(1-hydroxyethyl)-1,3,4-thiadiazol-2-yl]sulfamoyl] ethyl)-5-phenyl-1,2-oxazole-3-carboxamide as a white solid. LC-MS: [M+H]$^+$=424. The mixture was purified by Chiral-Prep-HPLC with the following conditions (Prep-HPLC-009): Column, Chiralpak IA, 2*25 cm, 5 um; mobile phase, Hex(0.1% IPA) and ethanol (hold 40.0% ethanol in 25 min); Detector, UV 254/220 nm. To give 30.4 mg (55%) of Isomer I as a white solid and 10.3 mg (19%) of Isomer II as a white solid.

Isomer I:

Analytical data: $^1$H NMR (400 MHz, CD$_3$OD, ppm): δ 7.90-7.88 (m, 2H), 7.56-7.50 (m, 3H), 7.08 (s, 1H), 4.93-4.90 (m, 2H), 3.87-3.83 (t, J=6.8 Hz, 2H), 3.43-3.38 (t, J=6.8 Hz, 2H), 1.53-1.51 (d, J=6.8 Hz, 3H).

HPLC purity: 99.7% at 254 nm.

Isomer II:

Analytical data: $^1$H NMR (400 MHz, CDCl$_3$, ppm): δ 7.90-7.87 (m, 2H), 7.57-7.50 (m, 3H), 7.10 (s, 1H), 5.00-4.92 (m, 2H), 3.86-3.83 (m, 2H), 3.38-3.34 (m, 2H), 1.52-1.50 (d, J=6.4 Hz, 3H).

HPLC purity: 99.6% at 254 nm.

Example 10: CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% CO$_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilized, the chambers are clamped, and data is recorded by pulse readings every 5 seconds. Following baseline current stabilization, the following additions can be applied and the changes in current and resistance of the cells can be monitored:

1. Benzamil to the apical chamber to inhibit ENaC sodium channel.
2. Forskolin to both chambers to activate ΔF508-CFTR by phosphorylation.
3. Genistein to both chambers to potentiate ΔF508-CFTR channel opening.
4. CFTRinh-172 to the apical chamber to inhibit ΔF508-CFTR Cl— conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% CO$_2$ for 24 hours. At the end of the treatment period, the media was changed to the Ieq experimental solution for 30 minutes before the experiment and plates are maintained in a CO$_2$-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:

1. The baseline $V_T$ and $G_T$ values were measured for approximately 20 minutes.
2. Benzamil was added to block ENaC for 15 minutes.
3. Forskolin plus VX-770 were added to maximally activate ΔF508-CFTR for 27 minutes.
4. Bumetanide was added to inhibit the NaK$_2$Cl cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples. The results are shown below in Table 2. (** indicates activity ≥200% of VX-809 (1 uM) with compound at 10 uM and VX-809 at 1 uM; * indicates activity 100-200% of VX-809 (1 uM) with compound at 10 uM and VX-809 at 1 uM. ## indicates activity ≥200% of VX-809 (3 uM) with compound at 10 uM and VX-809 at 3 uM; # indicates activity 100-200% of VX-809 (3 uM) with compound at 10 uM and VX-809 at 3 uM.

TABLE 2

| Compound | | Ieq activity |
|---|---|---|
| B1 | [structure] | ** |

TABLE 2-continued
| Compound | | Ieq activity |
|---|---|---|
| B2 (Example 2) | 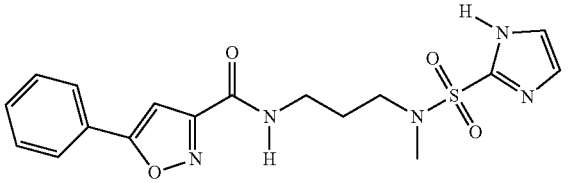 [SMILES: CN(CCCNC(=O)c1cc(-c2ccccc2)on1)S(=O)(=O)c1ncc[nH]1] | ** |
| B3 (Example 4) | 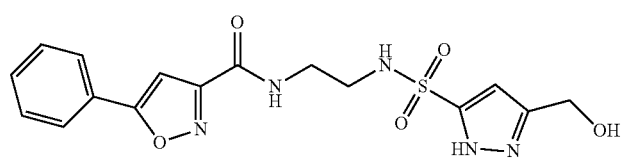 [SMILES: O=C(NCCNS(=O)(=O)c1cc(CO)n[nH]1)c1cc(-c2ccccc2)on1] | * |
| B4 (Example 5) | 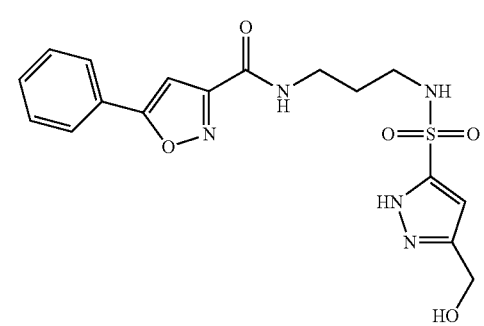 [SMILES: O=C(NCCCNS(=O)(=O)c1cc(CO)n[nH]1)c1cc(-c2ccccc2)on1] | ** |
| B5 (Example 6) | 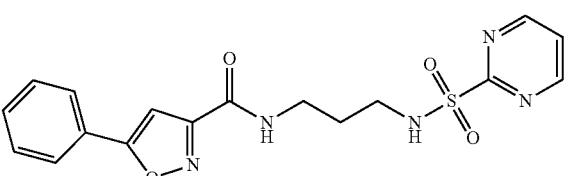 | ** |
| B6 (Example 7) | 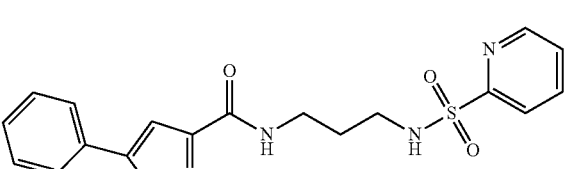 | ** |
| B7 (Example 8) | 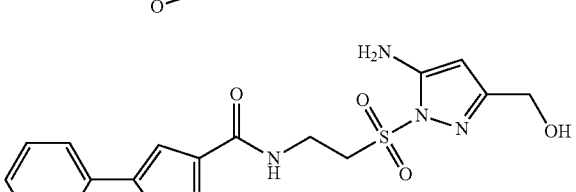 | * |
| B8 (Example 9) | 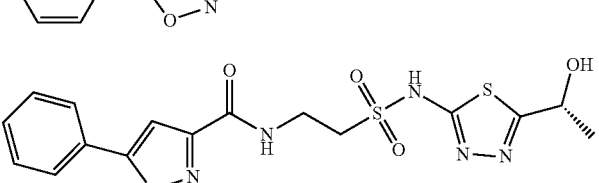 | * |
| B9 (Example 9) | 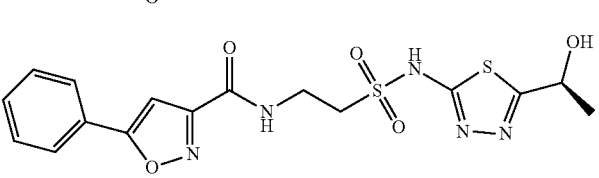 | * |

TABLE 2-continued

| Compound | | Ieq activity |
|---|---|---|
| B10 (Example 1) | 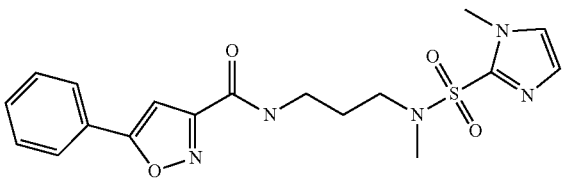 [SMILES: CN(CCCNC(=O)c1cc(-c2ccccc2)on1)S(=O)(=O)c1nccn1C] | ++, * |
| B11 (Example 3) | | ** |

Example 11 i. Ussing Measurements

As discussed above, Ussing measurements can be used to measure CFTR activity. In this method, primary lung epithelial cells (hBEs) with a Cystic fibrosis causing class I mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO or aqueous stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data are recorded by pulse readings every 5 seconds. Following baseline current stabilization, the following additions are applied and the changes in current and resistance of the cells are monitored:

1. Benzamil to the apical chamber to inhibit ENaC sodium channel.
2. Forskolin to both chambers to activate ΔF508-CFTR by phosphorylation.
3. Ivacaftor or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 12 i. Ussing Measurements

As discussed above, Ussing measurements can be used to measure CFTR activity. In this method, primary lung epithelial cells (hBEs) with a Cystic Fibrosis-causing class III mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:

1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 13 i. Ussing Measurements

As discussed above, Ussing measurements can be used to measure CFTR activity. In this method, primary lung epithelial cells (hBEs) with a Cystic Fibrosis-causing class V mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:

1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl— conductance.

The forskolin-sensitive current and inhibitable current (that potentiated current that is blocked by CFTRinh-172) are measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements are made following additions with standardized time periods:

1. The baseline $V_T$ and $G_T$ values are measured for approximately 20 minutes.
2. Benzamil is added to block ENaC for 15 minutes.
3. Forskolin plus VX-770 (ivacaftor) are added to maximally activate ΔF508-CFTR for 27 minutes.
4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

While this invention has been particularly shown and described with references to preferred embodiments thereof, it will be understood by those skilled in the art that various changes in form and details may be made therein without departing from the scope of the invention encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of treating a patient suffering from cystic fibrosis comprising administering to said patient an effective amount of a compound having the Formula (Ia) or (Ib):

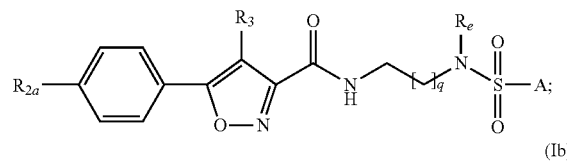

(Ia)

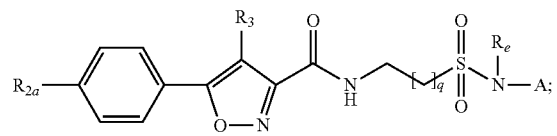

(Ib)

or a pharmaceutically acceptable salt, prodrug or solvate thereof, wherein:
$R_{2a}$ is hydrogen or fluoro;
$R_3$ is hydrogen or fluoro;
A is an optionally substituted 5- or 6-membered heteroaryl;
each $R_e$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and
q is 1 or 2.

2. The method of claim 1, wherein $R_3$ is hydrogen.

3. The method of claim 1, wherein $R_{2a}$ is hydrogen.

4. The method of claim 1, wherein $R_{2a}$ is fluoro.

5. The method of claim 1, wherein A is selected from the group consisting of furanyl, pyridinyl, pyrazinyl, pyridizanyl, pyrazolyl, imidazolyl, isoxazolyl, isothiazolyl, thiadiazolyl, triazolyl, thiazolyl, oxadiazolyl, thienyl, and benzimidazolyl, each optionally substituted.

6. The method of claim 5, wherein A is an optionally substituted imidazolyl or optionally substituted pyrazolyl.

7. The method of claim 1, wherein A is a 5- or 6-membered heteroaryl optionally substituted with one to four $R_6$, wherein:
each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, $C(O)OR_c$, $C(O)R_c$, $C(O)C(O)R_c$ and $S(O)_nR_c$;
each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and
each n is independently 0, 1 or 2.

8. The method of claim 1, wherein A is a 5- or 6-membered heteroaryl substituted with one to four $R_7$ groups, wherein:
each $R_7$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, halo, $OR_c$, $NR_dR_d$, $S(O)_nR_c$, $C(O)OR_c$, $NO_2$, CN and $C(O)R_c$, and wherein said 5- or 6-membered heteroaryl is optionally further substituted;
each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;
each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and
each n is independently 0, 1 or 2.

9. The method of claim 8, wherein at least one $R_7$ is selected from the group consisting of optionally substituted $C_1$-$C_{10}$ alkyl, optionally substituted $C_3$-$C_{12}$ cycloalkyl, and $OR_c$, wherein $R_c$ is an optionally substituted $C_1$-$C_{10}$ alkyl.

10. The method of claim 8, wherein at least one $R_7$ is $C_1$-$C_4$ alkyl or $C_3$-$C_7$ cycloalkyl, wherein the $C_1$-$C_4$ alkyl and $C_3$-$C_7$ cycloalkyl are each optionally substituted with one or more groups selected from $OR_f$, $NR_gR_g$, and $SR_h$,
wherein each of $R_f$ and $R_h$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and
$R_g$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or alternatively, two geminal $R_g$ groups are taken together with the nitrogen atom to which they are attached to form an optionally substituted heterocyclic or an optionally substituted heteroaryl.

11. The method of claim 8, wherein at least one of $R_7$ is $C_1$-$C_4$ alkyl optionally substituted with $OR_f$, wherein $R_f$ is selected from the group consisting of hydrogen, optionally substituted $C_1$-$C_{10}$ alkyl, and optionally substituted $C_3$-$C_{12}$ cycloalkyl.

12. The method of claim 11, wherein $R_f$ is hydrogen.

13. The method of claim 1, wherein the $R_7$ is a $C_1$-$C_4$ alkyl substituted with one or more fluoro, and optionally further substituted.

14. The method of claim 1, wherein A is a 5- or 6-membered heteroaryl substituted with at least one $R_8$ group having the structure:

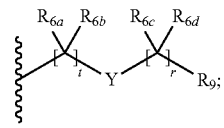

wherein $R_{6a}$, $R_{6b}$, $R_{6c}$, and $R_{6d}$ are each independently selected from the group consisting of hydrogen, optionally substituted $C_1$-$C_{10}$ alkyl and optionally substituted $C_3$-$C_{12}$ cycloalkyl; or alternatively, a geminal $R_{6a}$ and $R_{6b}$, or a geminal $R_{6c}$ and $R_{6d}$, can each independently be taken together with the carbon atoms to which they are attached to form an optionally substituted $C_3$-$C_{12}$ cycloalkyl or an optionally substituted heterocyclic;
Y is O, S or $NR_i$;
t and r are each independently 0, 1, 2 or 3;
$R_9$ is selected from the group consisting of optionally substituted $C_1$-$C_{10}$ alkyl and optionally substituted $C_3$-$C_{12}$ cycloalkyl, optionally substituted heterocyclic, optionally substituted aryl, and optionally substituted heteroaryl; and
$R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;
and wherein the 5- or 6-membered heteroaryl is optionally further substituted.

15. The method of claim 1, wherein $R_e$ is hydrogen or optionally substituted $C_1$-$C_4$ alkyl.

16. The method of claim 1, wherein q is 1.

17. The method of claim 1, wherein q is 2.

18. The method of claim 1, wherein the compound is selected from the group consisting of:

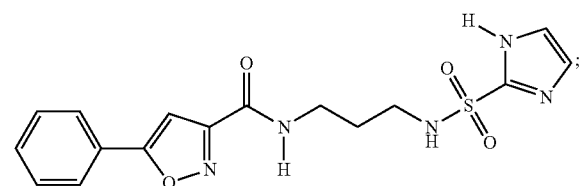

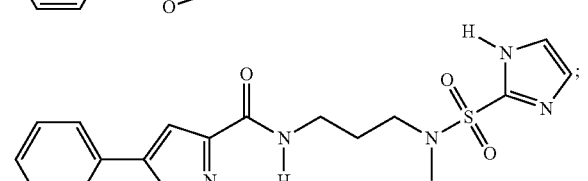

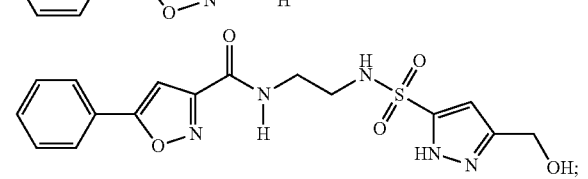

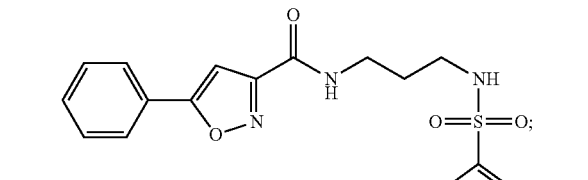

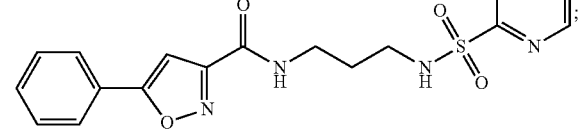

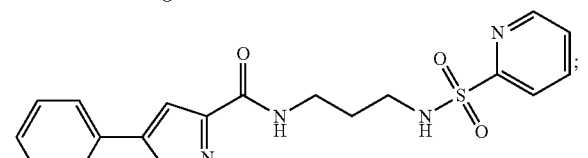

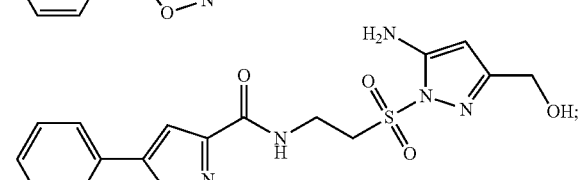

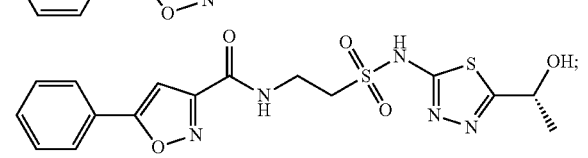

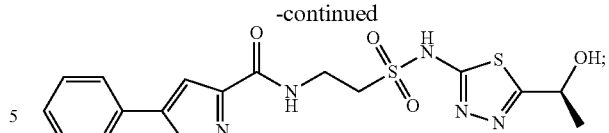

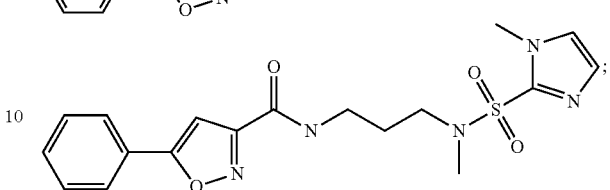

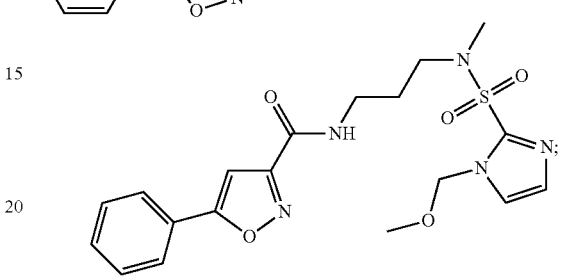

and a pharmaceutically acceptable salt thereof.

19. The method of claim 1, further comprising administering an additional therapeutic agent.

20. The method of claim 19, wherein at least two additional therapeutic agents are administered.

21. The method of claim 19, wherein at least one additional therapeutic agent is a CFTR corrector or potentiator.

22. The method of claim 21, wherein each CFTR corrector or potentiator is independently selected from the group consisting of VX-770 (Ivacaftor), VX-809 (3-(6-(1-(2,2-difluorobenzo[d][1,3]dioxol-5-yl)cyclopropanecarboxamido)-3-methylpyridin-2-yl)benzoic acid), VX-661 ((R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane-1-carboxamide), GLPG-2222, and GLPG-1837.

23. A method of treating a patient suffering from cystic fibrosis comprising administering to said patient an effective amount of a compound represented by:

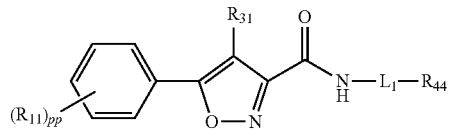

or a pharmaceutically acceptable salt, prodrug or solvate thereof, wherein pp is 1, 2, or 3;

$R_{11}$ is independently selected for each occurrence from the group consisting of hydrogen, halogen, $C_{1-4}$ alkyl (optionally substituted by one, two or three halogens);

$R_{31}$ is selected from the group consisting of hydrogen, halogen, and $C_{1-4}$ alkyl;

$L_1$ is selected from the group consisting of $C_{2-3}$ alkylene-$NR_{hh}$—S(O)$_w$- and —$C_{1-3}$ alkylene-S(O)$_w$—$NR_{hh}$—, wherein w is 0, 1, or 2, and $L_1$ may be optionally substituted by one, two or three substituents selected from the group consisting of halogen, hydroxyl, $C_{1-3}$ alkyl (optionally substituted by one, two or three substituents each selected independently from $R_{ff}$);

$R_{44}$ is selected from the group consisting of heterocycle and a 5-6 membered monocyclic heteroaryl having one, two or three heteroatoms each selected from O, N, and S; wherein the heterocycle and the heteroaryl may be each optionally substituted by one or two substituents each selected independently from the group consisting of halogen, hydroxyl, $C_{1-6}$ alkyl, $C_{1-6}$ alkoxy, $C_{2-6}$ alkenyl, $C_{2-6}$ alkynyl, and $C_{3-7}$ cycloalkyl, wherein each of $C_{1-6}$ alkyl, $C_{1-6}$ alkoxy, $C_{2-6}$ alkenyl, $C_{2-6}$ alkynyl, and $C_{3-7}$ cycloalkyl may be optionally substituted by one, two or three substituents each independently selected from $R_{gg}$;

$R_{gg}$ is selected from the group consisting of halogen, $C_{1-6}$ alkyl, $C_{1-6}$ alkoxy, hydroxyl, C(O)OH, —C(O)O$C_{1-6}$ alkyl, —O—$C_{3-6}$ cycloalkyl, —O-heterocycle, —O-heteroaryl, —O-phenyl, —NR'R", —NR'—S(O)$_w$—$C_{1-3}$ alkyl, S(O)$_w$—NR'R", and —S(O)$_w$—$C_{1-3}$ alkyl wherein w is 0, 1, or 2;

$R_{ff}$ is selected for each occurrence from group consisting of halogen, hydroxyl, $C_{1-4}$ alkyl, $C_{1-4}$ alkoxy, $C_{2-4}$ alkenyl, $C_{3-6}$ cycloalkyl, —NR'R", —NR'—S(O)$_w$—$C_{1-3}$ alkyl, S(O)$_w$—NR'R", and —S(O)$_w$—$C_{1-3}$ alkyl, where w is 0, 1, or 2, wherein $C_{1-4}$ alkyl, $C_{1-4}$ alkyoxy, $C_{2-4}$ alkenyl and $C_{3-6}$ cycloalkyl may be optionally substituted by one, two or three substituents each independently selected from the group consisting of halogen, hydroxyl, —NR'R", —NR'—S(O)$_w$—$C_{1-3}$ alkyl, S(O)$_w$—NR'R", and —S(O)$_w$—$C_{1-3}$ alkyl;

$R_{hh}$ is selected for each occurrence from the group consisting of H, $C_{1-6}$ alkyl and $C_{3-6}$ cycloalkyl; and R' and R" are each independently selected for each occurrence from H and $C_{1-4}$ alkyl or taken together with the nitrogen to which they are attached form a heterocyclic ring.

24. The method of claim 23, wherein $R_{44}$ is selected from the group consisting of:

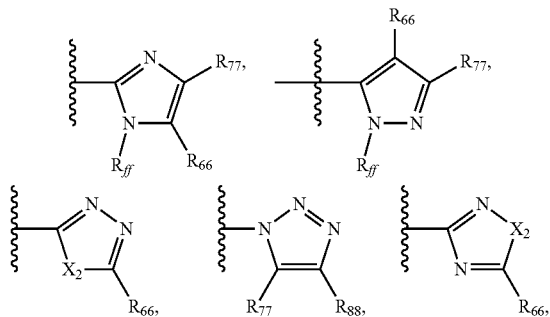

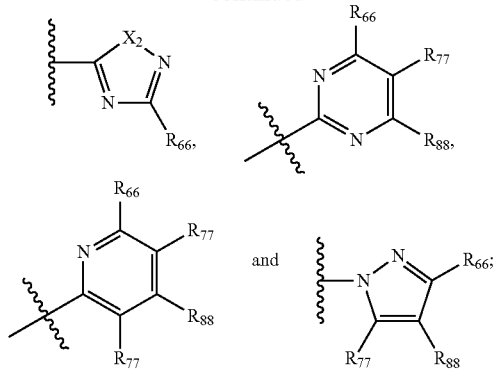

wherein $X_2$ independently for each occurrence is selected from the group consisting of O, S or $NR_{hh}$; and each $R_{66}$, $R_{77}$ and $R_{88}$ is independently selected for each occurrence from H, halogen, hydroxyl, and $C_{1-6}$ alkyl, wherein $C_{1-6}$ alkyl is optionally substituted by one, two or three substituents each independently selected from the group consisting of hydroxyl or $C_{1-6}$ alkoxy.

25. The method of claim 23, wherein $R_{44}$ is 5 or 6 membered heteroaryl having one or two nitrogens, and wherein $R_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy.

26. The method of claim 23, wherein $R_{11}$ for each occurrence is H.

27. The method of claim 23, wherein $R_{31}$ is H.

28. The method of claim 23, wherein $L_1$ is $C_{2-3}$ alkylene-NH—S(O)$_2$- or —$C_{1-3}$ alkylene-S(O)$_2$—NH—.

* * * * *